(12) United States Patent
Basrur et al.

(10) Patent No.: US 8,987,483 B2
(45) Date of Patent: Mar. 24, 2015

(54) METHOD OF STARTING-UP A PROCESS OF PRODUCING AN ALKYLENE OXIDE USING A HIGH-EFFICIENCY CATALYST

(75) Inventors: Arun G. Basrur, Pune (IN); Ravindra R. Tupe, Pune (IN); Hwaili Soo, Charleston, WV (US); Paul V. Hinman, Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 13/994,233

(22) PCT Filed: Dec. 1, 2011

(86) PCT No.: PCT/US2011/062856
§ 371 (c)(1),
(2), (4) Date: Oct. 2, 2013

(87) PCT Pub. No.: WO2012/082389
PCT Pub. Date: Jun. 21, 2012

(65) Prior Publication Data
US 2014/0024846 A1    Jan. 23, 2014

Related U.S. Application Data

(60) Provisional application No. 61/423,238, filed on Dec. 15, 2010.

(51) Int. Cl.
*C07D 301/03* (2006.01)
*C07D 301/10* (2006.01)

(52) U.S. Cl.
CPC .................................. *C07D 301/10* (2013.01)
USPC ......................................................... 549/536

(58) Field of Classification Search
CPC ..................................................... C07D 301/10
USPC ........................................................... 549/536
See application file for complete search history.

(56) References Cited

U.S. PATENT DOCUMENTS

| 5,155,242 A | 10/1992 | Shankar et al. |
| 6,717,001 B2 | 4/2004 | Evans et al. |
| 7,102,022 B2 | 9/2006 | Evans et al. |
| 2004/0049061 A1 | 3/2004 | Lockemeyer et al. |
| 2004/0236124 A1 | 11/2004 | Evans et al. |

(Continued)

FOREIGN PATENT DOCUMENTS

| EP | 0567273 A1 | 10/1993 |
| EP | 0352850 B1 | 1/1994 |

(Continued)

OTHER PUBLICATIONS

International Preliminary Report on Patentability dated, Jun. 10, 2013.

(Continued)

*Primary Examiner* — T. Victor Oh
(74) *Attorney, Agent, or Firm* — Hansen IP Law PLLC

(57) ABSTRACT

A method for starting-up a high efficiency alkylene oxide catalyst is described. A feed gas comprising an alkylene, oxygen, and at least one organic chloride is introduced to the catalyst. The molar ratio of oxygen to alkylene, reaction temperature, and overall chloriding effectiveness are adjusted to specified ranges of values within a specified catalyst aging period.

15 Claims, 11 Drawing Sheets

(56) References Cited

U.S. PATENT DOCUMENTS

| | | |
|---|---|---|
| 2007/0185339 A1 | 8/2007 | Lu |
| 2008/0281118 A1 | 11/2008 | Matusz |
| 2008/0306291 A1 | 12/2008 | Billig et al. |

FOREIGN PATENT DOCUMENTS

| | | |
|---|---|---|
| EP | 1458699 B1 | 11/2005 |
| WO | 9505896 A1 | 3/1995 |
| WO | 2004002971 A1 | 1/2004 |
| WO | 2009042300 A1 | 4/2009 |
| WO | 2010123842 A1 | 10/2010 |

OTHER PUBLICATIONS

International Search Report and Written Opinion dated, Mar. 30, 2012.
Response to Written Opinion As-Filed dated, Sep. 21, 2012.
International Preliminary Examining Authority (IPEA) Written Opinion dated, Mar. 6, 2013.
Response to IPEA Written Opinion As-Filed dated, Apr. 11, 2013.

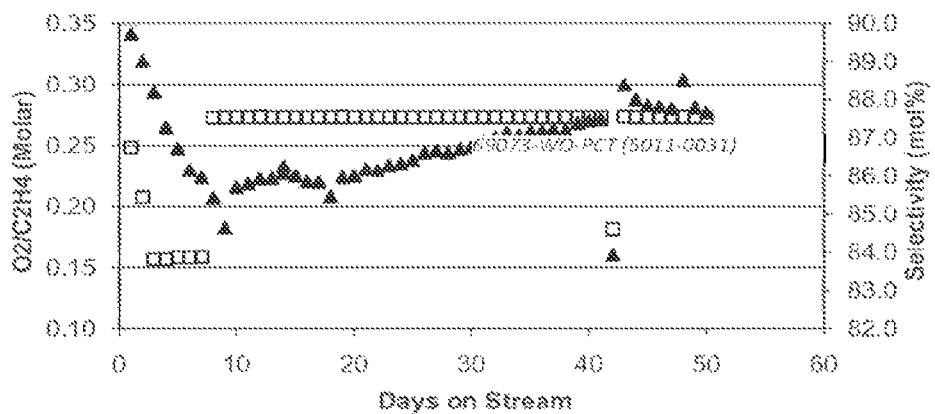
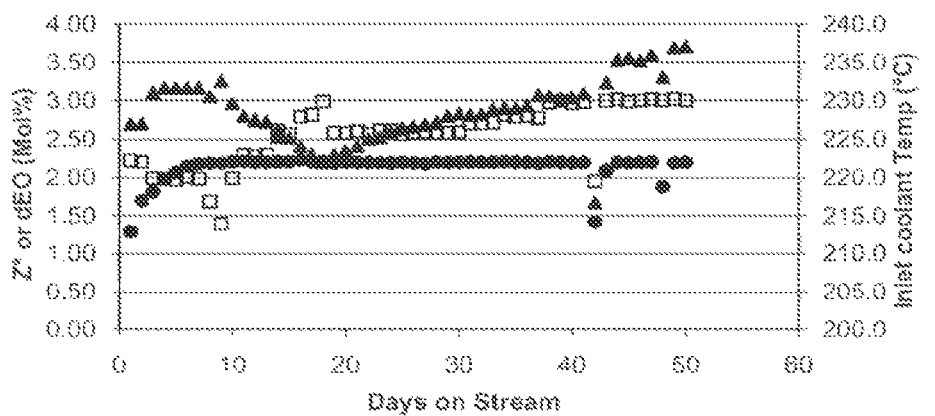

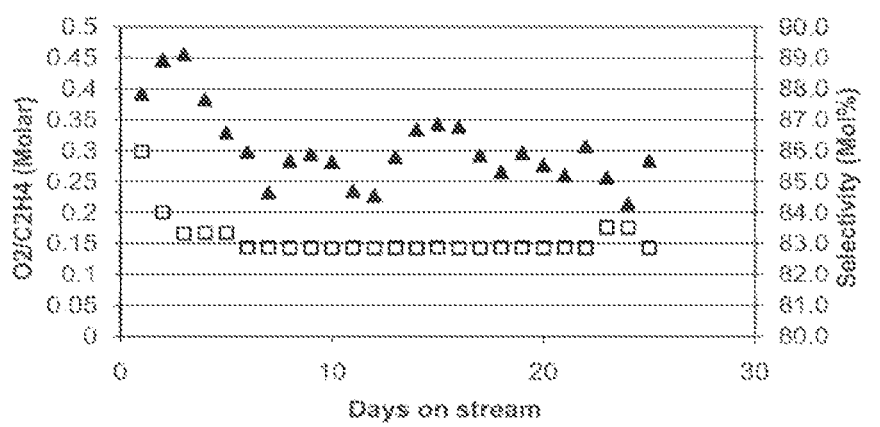
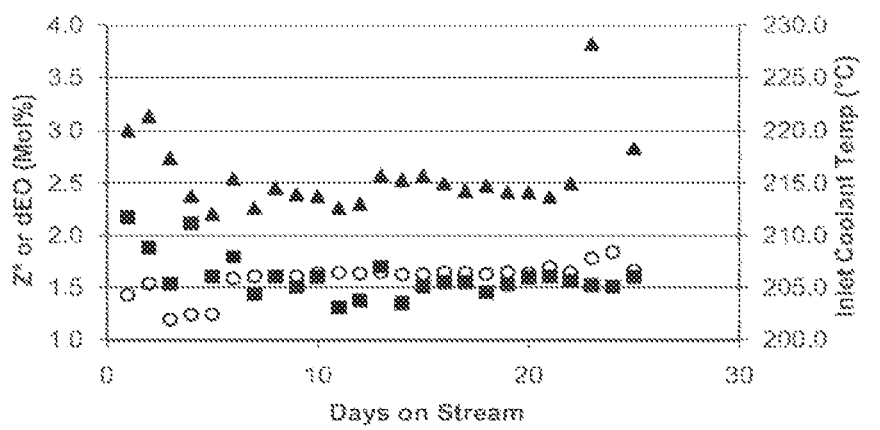

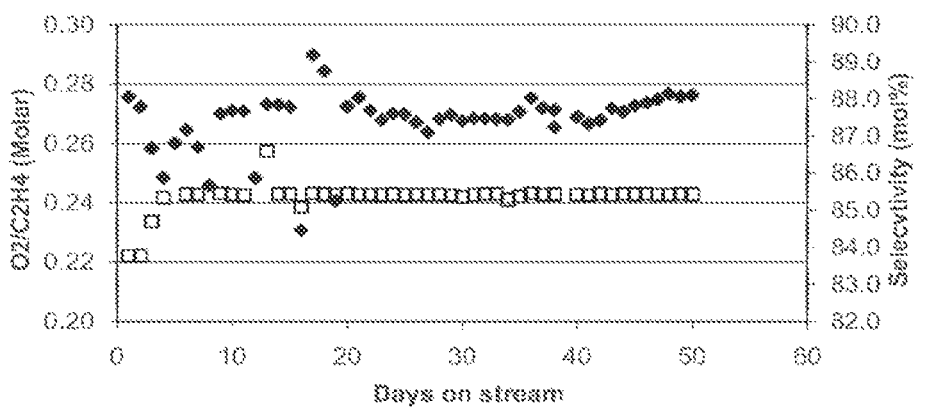
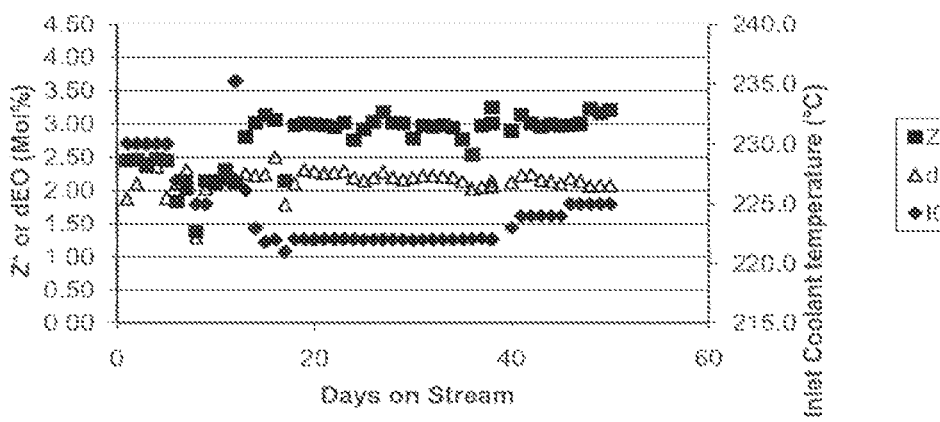

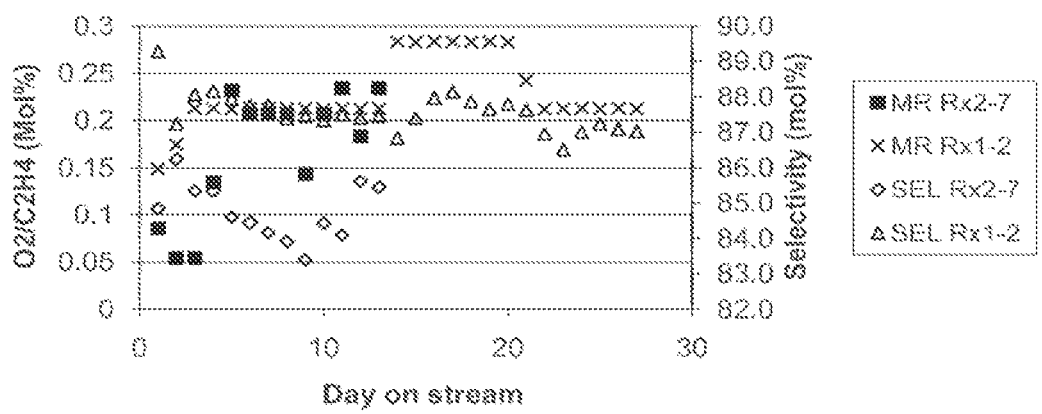
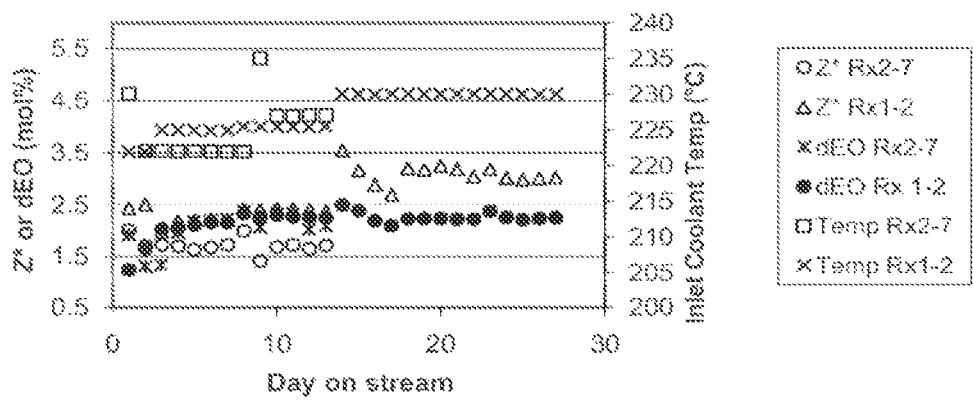

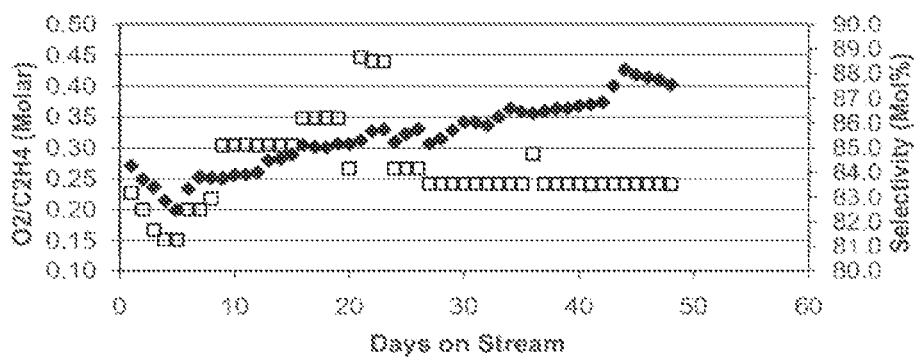
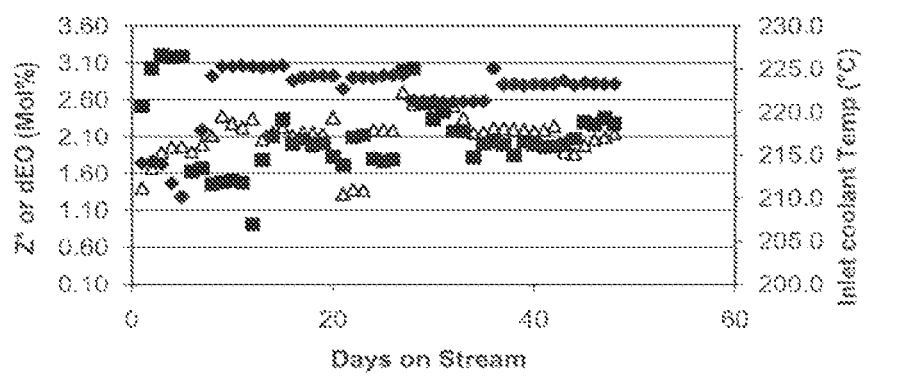

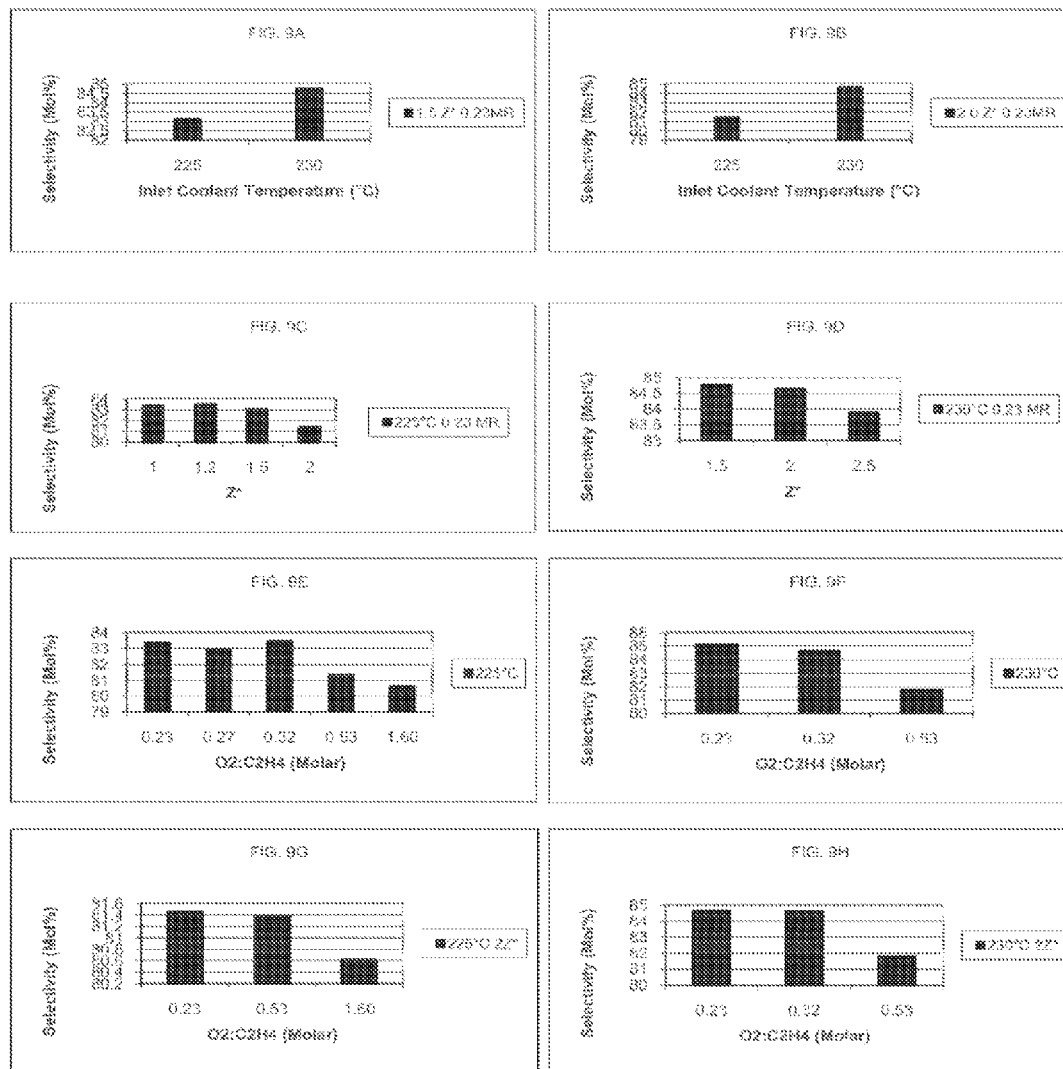

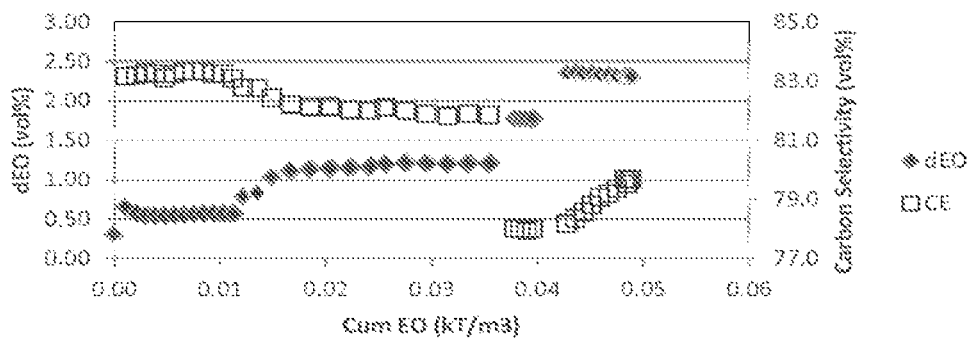
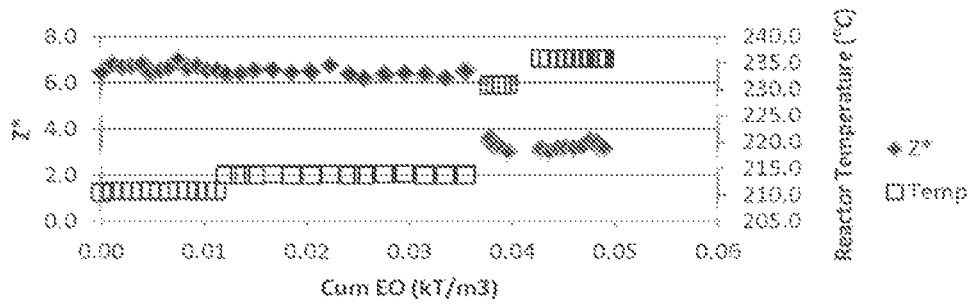

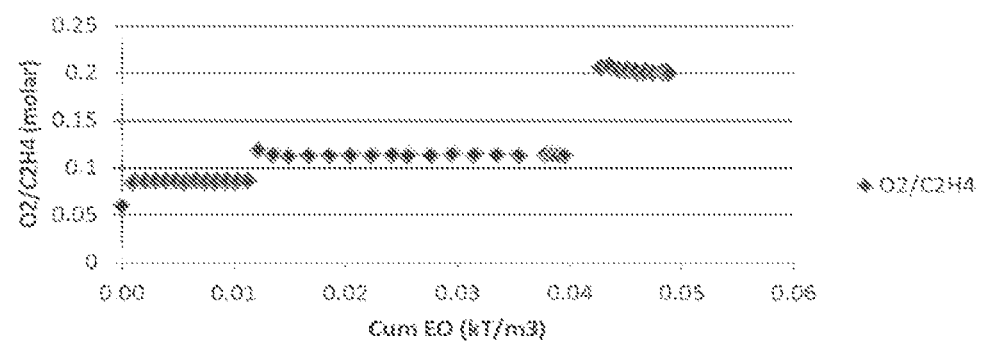

METHOD OF STARTING-UP A PROCESS OF PRODUCING AN ALKYLENE OXIDE USING A HIGH-EFFICIENCY CATALYST

TECHNICAL FIELD

This disclosure relates generally to processes for making alkylene oxides, and more specifically, to a method of starting up a process for making an alkylene oxide using a high-efficiency catalyst.

BACKGROUND

The production of alkylene oxides via catalytic epoxidation of olefins in the presence of oxygen using silver based catalysts is known. Conventional silver-based catalysts used in such processes typically provide a relatively lower efficiency or "selectivity" (i.e., a lower percentage of the reacted alkylene is converted to the desired alkylene oxide). In certain exemplary processes, when using conventional catalysts in the epoxidation of ethylene, the theoretically maximal efficiency towards ethylene oxide, expressed as a fraction of the ethylene converted, does not reach values above the 6/7 or 85.7 percent limit. Therefore, this limit had long been considered to be the theoretically maximal efficiency of this reaction, based on the stoichiometry of the following reaction equation:

$$7C_2H_4 + 6O_2 \rightarrow 6C_2H_4O + 2CO_2 + 2H_2O$$

cf. Kirk-Othmer's Encyclopedia of Chemical Technology, 4th ed., Vol. No. 9, 1994, p. 926.

Certain "high efficiency" or "high selectivity" modern silver-based catalysts are highly selective towards alkylene oxide production. For example, when using certain modern catalysts in the epoxidation of ethylene, the theoretically maximal efficiency towards ethylene oxide can reach values above the 6/7 or 85.7 percent limit referred to, for example 88 percent or 89 percent, or above. As used herein, the terms "high efficiency catalyst" and "high selectivity catalyst" refer to a catalyst that is capable of producing an alkylene oxide from the corresponding alkylene and oxygen at an efficiency greater than 85.7 percent. The observed actual efficiency of a high efficiency catalyst may fall below 85.7 percent under certain conditions based on process variables, catalyst age, etc. However, if the catalyst is capable of achieving at least an 85.7 percent efficiency, it is considered to be a high efficiency catalyst. Such highly efficient catalysts, which may comprise as their active components silver, rhenium, at least one further metal, and optionally, a rhenium co-promoter, are disclosed in EP0352850B1 and in several subsequent patent publications.

"Promoters," sometimes referred to as "inhibitors" or "moderators," refer to materials that enhance the performance of the catalysts by either increasing the rate towards the desired formation of alkylene oxide and/or suppressing the undesirable oxidation of olefin or alkylene oxide to carbon dioxide and water, relative to the desired formation of alkylene oxide. As used herein, the term "co-promoter" refers to a material that—when combined with a promoter—increases the promoting effect of the promoter. In addition, promoters may also be referred to as "dopants." In the case of those promoters that provide high efficiencies, the terms "high efficiency dopants" or "high selectivity dopants" may be used.

"Promoters" can be materials that are introduced to catalysts during the preparation of the catalysts (solid phase promoters). In addition, "promoters" can also be gaseous materials that are introduced to the epoxidation reactor feed (gas phase promoters). In one example, an organic halide gas phase promoter may be added continuously to the epoxidation reactor feed to increase the catalyst efficiency. For silver-based ethylene epoxidation catalysts, both solid and gas phase promoters are typically required in any commercial processes.

Conventional catalysts have relatively flat efficiency curves with respect to the gas phase promoter concentration in the feed at a constant alkylene oxide production rate, i.e., the efficiency is almost invariant (i.e., the change in efficiency with respect to a change in gas phase promoter concentration in the feed at a constant alkylene oxide production rate is less than 0.1%/ppm) over a wide range of promoter concentrations, and this invariance is substantially unaltered as reactor temperature is changed (i.e., the change in efficiency with respect to a change in reactor temperature at a constant alkylene oxide production rate is less than 0.1%/° C.) during prolonged operation of the catalyst. However, conventional catalysts have nearly linear activity decline curves with respect to the gas phase promoter concentration in the feed, i.e., with increasing gas phase promoter concentration in the feed, temperature has to be increased or the alkylene oxide production rate will be reduced.

By contrast, high efficiency catalysts tend to exhibit relatively steep efficiency curves as a function of gas phase promoter concentration as the concentration moves away from the value that provides the highest efficiency (i.e., the change in efficiency with respect to a change in gas phase promoter concentration is at least 0.2%/ppm when operating away from the efficiency maximizing concentration). Thus, small changes in the promoter concentration can result in significant efficiency changes, and the efficiency exhibits a pronounced maximum, i.e., an optimum, at certain concentrations (or feed rates) of the gas phase promoter for a given reaction temperature and catalyst age. Moreover, the efficiency curves and the optimum gas phase promoter concentration tend to be strong functions of reactor temperature and are thus significantly affected if reactor temperature is varied, for example, to compensate for decreases in catalyst activity, (i.e., the change in efficiency with respect to a change in reactor temperature can be at least 0.1%/° C. when operating away from the efficiency maximizing promoter concentrations for the selected temperatures). In addition, high efficiency catalysts have exhibited significant activity increases with increases in the gas phase promoter concentration in the feed, i.e., with increasing gas phase promoter concentration in the feed, temperature has to be decreased or the production rate will increase.

The performance of high-efficiency catalysts can be significantly affected by the process conditions under which alkylene oxide production is started up. In certain cases, a poor choice of start-up conditions may prevent the catalyst from achieving the performance that it would otherwise be able to achieve. In addition, the dynamic variation in start-up conditions may also affect catalyst performance. Thus, a need has arisen for a method of starting-up a high efficiency alkylene oxide catalyst.

SUMMARY

A method for starting-up an alkylene oxide production process is provided. The process comprises reacting a feed gas comprising an alkylene, oxygen, and at least one organic chloride over a high-efficiency silver catalyst to yield a reaction product comprising the alkylene oxide. The start-up method comprises providing a feed gas comprising the alkylene, oxygen, and the at least one organic chloride, wherein the feed gas has an overall chloriding effectiveness represented by the formula:

$$Z^* = \frac{\text{ethyl chloride equivalent}(ppmv)}{\text{ethane equivalent (mole \%)}}$$

wherein, the ethyl chloride equivalent is the total concentration in ppmv of ethyl chloride which provides substantially the same catalyst chloriding effectiveness of the at least one organic chloride in the feed gas at the concentration of the at least one organic chloride in the feed gas, and the ethane equivalent is the total concentration in mole % of ethane which provides substantially the same dechloriding effectiveness as the non-chloride containing hydrocarbons in the feed gas at the concentration of the non-chloride containing hydrocarbons in the feed gas. The feed gas has a Z* value ranging from 1.0 to 5.0. The start-up method further comprises reacting the feed gas over the high-efficiency silver catalyst at a reaction temperature such that within a catalyst aging period of no greater than 0.03 kT alkylene oxide/m³ catalyst after the reactor is first on-stream, the reaction temperature is from 215° C. to 240° C., and the molar ratio of oxygen to the alkylene in the feed gas is at least 0.2, thereby yielding a reaction product comprising a start up concentration of the alkylene oxide.

A method for producing an alkylene oxide by reacting an alkylene, oxygen, and at least one organic chloride over a high efficiency silver catalyst is also provided. The method comprises reacting a feed gas comprising the alkylene, oxygen, and at least one organic chloride over the high-efficiency silver catalyst at a reaction temperature and an overall chloriding effectiveness to yield a reaction product comprising the alkylene oxide such that the process has a molar ratio of oxygen to the alkylene in the feed gas and a first efficiency to the alkylene oxide, the first efficiency to the alkylene oxide being less than a desired efficiency to the alkylene oxide. At least one process parameter is adjusted such that the efficiency of the process to the alkylene oxide increases from the first efficiency to a second efficiency. The at least one process parameter is selected from the group consisting of the molar ratio of oxygen to the alkylene in the feed gas, reactor temperature, and overall chloriding effectiveness. Following the adjusting step, the molar ratio of oxygen to the alkylene in the feed gas is at least 0.2, the reaction temperature is from 215° C. to 240° C., and the overall chloriding effectiveness is represented as Z* and is from 1.0 to 5.0, wherein Z* is represented as follows:

$$Z^* = \frac{\text{ethyl chloride equivalent}(ppmv)}{\text{ethane equivalent (mole \%)}}$$

wherein the ethyl chloride equivalent is the total concentration in ppmv of ethyl chloride which provides substantially the same catalyst chloriding effectiveness of the at least one organic chloride in the feed gas at the concentration of the at least one organic chloride in the feed gas, and the ethane equivalent is the total concentration in mole % of ethane which provides substantially the same dechloriding effectiveness as the non-chloride containing hydrocarbons in the feed gas at the concentration of the non-chloride containing hydrocarbons in the feed gas.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

FIG. 4A is a graph depicting the effect of lowering and subsequently increasing the start-up molar ratio of oxygen to ethylene on the efficiency to ethylene oxide in an experimental process of making ethylene oxide with a high efficiency catalyst;

FIG. 4B is a graph depicting inlet coolant temperature, overall chloriding effectiveness (Z*) and ΔEO data for the experimental process of FIG. 4A;

FIG. 5A is a graph depicting the effect of lowering the start-up molar ratio of oxygen to ethylene on the efficiency to ethylene oxide in an experimental process of making ethylene oxide with a high efficiency catalyst;

FIG. 5B is a graph depicting inlet coolant temperature, overall chloriding effectiveness (Z*) and ΔEO data for the experimental process of FIG. 5A;

FIG. 6A is a graph depicting the effect of maintaining a high start-up molar ratio of oxygen to ethylene on the efficiency to ethylene oxide in an experimental process of making ethylene oxide with a high efficiency catalyst;

FIG. 6B is a graph depicting inlet coolant temperature, overall chloriding effectiveness (Z*) and ΔEO data for the experimental process of FIG. 6A;

FIG. 7A is a graph depicting the effect of a relatively low and relatively high start-up molar ratio of oxygen to ethylene on the efficiency to ethylene oxide in two experimental processes of making ethylene oxide with high-efficiency catalysts;

FIG. 7B is a graph depicting inlet coolant temperature, overall chloriding effectiveness (Z*) and ΔEO data for the experimental processes of FIG. 7A;

FIG. 8A is a graph depicting selectivity (efficiency) and the molar ratio of oxygen to ethylene for a method of reviving a high-efficiency catalyst in an experimental process for making ethylene oxide;

FIG. 8B is a graph depicting inlet coolant temperature, overall chloriding effectiveness (Z*) and ΔEO data for the experimental process of FIG. 8A;

FIG. 9A is a graph depicting the effect of inlet coolant temperature on the efficiency to ethylene oxide of a high efficiency ethylene oxide catalyst at an overall catalyst chloriding value, Z*, of 1.5 and a molar ratio of oxygen to ethylene in the feed gas of 0.23;

FIG. 9B is a graph depicting the effect of inlet coolant temperature on the efficiency to ethylene oxide of a high efficiency ethylene oxide catalyst at an overall catalyst chloriding value, Z*, of 2.0 and a molar ratio of oxygen to ethylene in the feed gas of 0.23;

FIG. 9C is a graph depicting the effect of varying the overall catalyst chloriding value, Z*, on the efficiency to ethylene oxide of a high efficiency ethylene oxide catalyst at a inlet coolant temperature of 225° C. and a molar ratio of oxygen to ethylene in the feed gas of 0.23;

FIG. 9D is a graph depicting the effect of varying the overall catalyst chloriding value, Z*, on the efficiency to ethylene oxide of a high efficiency ethylene oxide catalyst at a inlet coolant temperature of 230° C. and a molar ratio of oxygen to ethylene in the feed gas of 0.23;

FIG. 9E is graph depicting the effect of varying the molar ratio of oxygen to ethylene on the efficiency to ethylene oxide of a high efficiency ethylene oxide catalyst at a inlet coolant temperature of 225° C. and a variable overall catalyst chloriding value, Z*, in the range of 1.0-2.0;

FIG. 9F is a graph depicting the effect of varying the molar ratio of oxygen to ethylene on the efficiency to ethylene oxide of a high efficiency ethylene oxide catalyst at a reactor coolant inlet temperature of 230° C. and a variable overall catalyst chloriding value, Z*, in the range of 1.0-2.0;

FIG. 9G is a graph depicting the effect of varying the molar ratio of oxygen to ethylene on the efficiency to ethylene oxide of a high efficiency ethylene oxide catalyst at a inlet coolant temperature of 225° C. and an overall catalyst chloriding value, Z*, of 2.0;

FIG. 9H is a graph depicting the effect of varying the molar ratio of oxygen to ethylene on the efficiency to ethylene oxide of a high efficiency ethylene oxide catalyst at a inlet coolant temperature of 230° C. and an overall catalyst chloriding value, Z*, of 2.0;

FIG. 10A is a graph depicting the efficiency to ethylene oxide of a high efficiency ethylene oxide catalyst and ΔEO in a process for making ethylene oxide at various cumulative ethylene oxide work rates as a result of the variable changes depicted in FIGS. 10B and 10C;

FIG. 10B is a graph depicting the overall catalyst chloriding effectiveness (Z*) and inlet coolant temperature at various cumulative ethylene oxide work rates in the process of FIG. 10A; and FIG. 10C is a graph depicting the ratio of oxygen to ethylene at various cumulative ethylene oxide work rates in the process of FIG. 10A.

DETAILED DESCRIPTION

Figure 1:
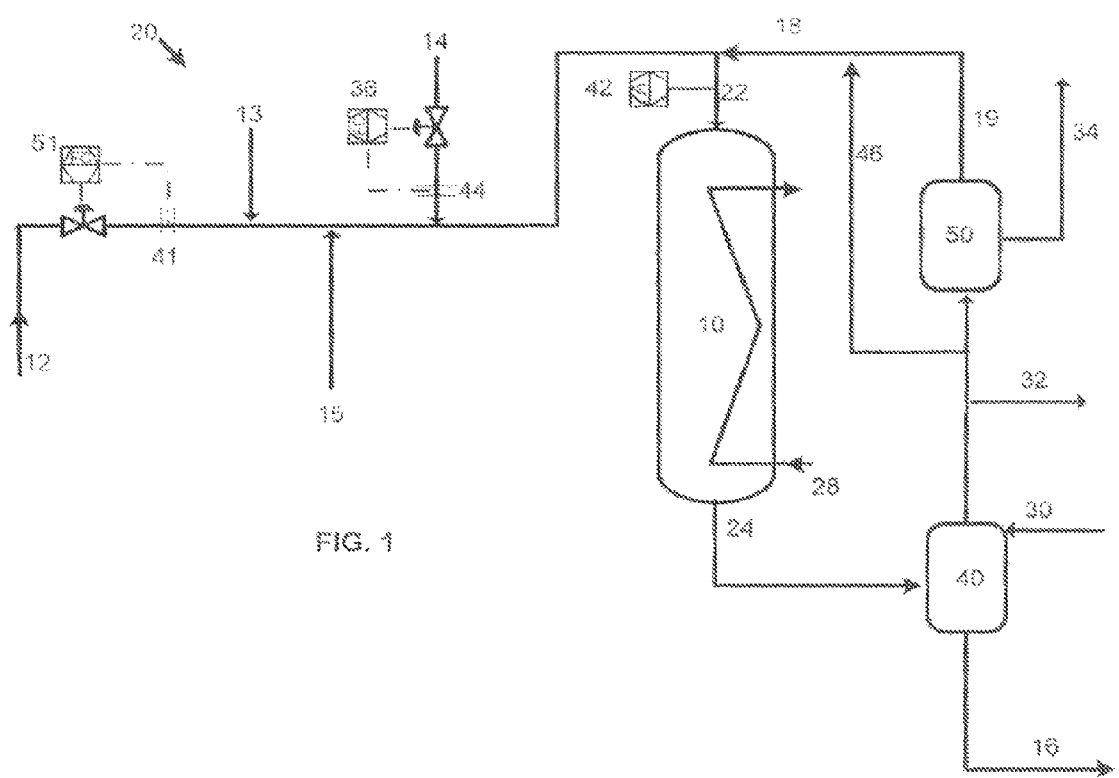
FIG. 1 is a process flow diagram depicting an embodiment of a process for making an alkylene oxide by epoxidizing an olefin over a high efficiency catalyst.

As discussed below, the present disclosure provides a method for starting up a high efficiency silver catalyst in a process for making an alkylene oxide by reacting an alkylene, oxygen, and at least one organic chloride over the catalyst. The method involves the combination of selected values of the ratio of oxygen to alkylene in the feed gas, reaction temperature, and overall chloriding effectiveness and achieving the selected values within a certain catalyst aging period after the reactor is first on-stream. As used herein, the phrase "first on-stream" refers to the point in time at which an aged or fresh high-efficiency silver catalyst begins producing an alkylene oxide following a period of non-production of alkylene oxide. The phrase "start-up" refers to a process that begins when an aged or fresh catalyst is first subjected to a reactive mixture comprising an alkylene, at least one organic chloride, and oxygen following a period during which the catalyst is not subjected to such a reactive mixture. Start-up is typically considered to be complete when the process reaches steady-state, i.e., when one or more variables of interest reach sustained, constant values or fluctuate by no more than a selected maximum amount.

The present disclosure also provides a method of reviving the performance of a high-efficiency silver catalyst in a process for making an alkylene oxide by reacting an alkylene, oxygen, and at least one organic chloride over the catalyst. The method involves adjusting at least one process parameter selected from the group consisting of the molar ratio of oxygen to alkylene in the feed gas, reaction temperature, and overall chloriding effectiveness (Z*) to certain values described herein.

In order to facilitate an understanding of the present disclosure, it is useful to define certain terms relating to catalyst and process performance. The activity of a catalyst in a fixed bed reactor is generally defined as the reaction rate towards the desired product per unit of catalyst volume in the reactor. The activity relates to both the total number of available active sites and the reaction rate of each site. "Activity" can be quantified in a number of ways, one being the mole % of alkylene oxide contained in the outlet stream of the reactor relative to that in the inlet stream (the mole % of alkylene oxide in the inlet stream typically, but not necessarily, approaches zero percent) while the reactor temperature is maintained substantially constant; and another being the temperature required to maintain a given rate of alkylene oxide production. In many instances, activity is measured over a period of time in terms of the mole % of alkylene oxide produced at a specified constant temperature. Alternatively, activity may be measured as a function of the temperature required to sustain production of a specified constant mole % of alkylene oxide, such as ethylene oxide, given other conditions such as pressure and total moles in the feed.

The "efficiency" of the epoxidation, which is synonymous with "selectivity," refers to the relative amount (as a fraction or in percent) of converted or reacted olefin that forms a particular product. For example, the "efficiency to alkylene oxide" refers to the percentage on a molar basis of converted or reacted olefin that forms alkylene oxide. The "yield" of alkylene oxide refers to the net number of moles of alkylene oxide produced by the process divided by the net number of moles of olefin fed to the process for any given time period.

The term "alkylene oxide production parameter" is used herein to describe a variable that relates to the extent to which alkylene oxides are produced. Examples of alkylene oxide production parameters include, without limitation, alkylene oxide concentration, alkylene oxide yield, alkylene oxide production rate, alkylene oxide production rate/catalyst volume, alkylene conversion, and oxygen conversion. Thus, the alkylene oxide concentration relates to the alkylene oxide production rate because the production rate may be obtained by multiplying the alkylene oxide concentration and the net product flow rate. The alkylene oxide production rate/catalyst volume may be determined by dividing the production rate by the volume of the catalyst bed. The oxygen and alkylene conversions are related to the production of the alkylene oxide by the efficiency.

As is known in the art, as a reaction is carried out over a catalyst over a period of time, the catalyst eventually begins to "age" and lose activity, which typically means that the number of active sites available for catalyzing the desired reaction are reduced. One measure of catalyst aging is the total production of alkylene oxide on a mass basis (e.g., using metric kilotons "kT") divided by the catalyst-packed reactor volume (e.g., in cubic meters). Another measure of catalyst aging is the total production of alkylene oxide on a molar basis divided by the catalyst-packed reactor volume. As used herein, the term "fresh catalyst" means a catalyst that has not aged or which has aged by an amount no greater than 0.02 kT alkylene oxide/cubic meter of catalyst. The term "fresh catalyst" includes catalysts that have not yet been exposed to a reactive epoxidation feed gas. However, the term also includes and more broadly refers to catalysts that have not aged beyond the aging threshold of 0.02 kT alkylene oxide/cubic meter of catalyst. The term "catalyst aging period" refers to an incremental change in catalyst age occurring between two points in time. Where a catalyst has an initial age, $A_i$ and ages to a subsequent age, $A_{i+1}$, the catalyst aging period is $A_{i+1}-A_i$. Put differently, a "catalyst aging period" is the incremental amount of alkylene oxide produced between two points in time divided by the catalyst-packed reactor volume.

FIG. 1 illustrates a process 20 for making an alkylene oxide. Process 20 includes a reactor 10 comprising a tubular vessel with a catalyst bed disposed in it. Olefin (i.e., alkylene) feed stream 12 (which may also include saturated hydrocarbons, such as ethane, as an impurity) is combined with ballast gas 13, oxygen feed 15 and gas phase promoter feed 14 to define reactor feed gas inlet stream 22 proximate the reactor inlet. Reactor product stream 24 includes the alkylene oxide ("AO") product, plus side products (e.g., $CO_2$, $H_2O$, and small amounts of saturated hydrocarbons and organic chloride products), unreacted olefin, unreacted organic chloride, oxygen, and inerts. Water stream 30 is added to alkylene oxide absorber 40 to absorb alkylene oxide product from reactor product stream 24. Net product stream 16 comprises water and alkylene oxide, and the alkylene oxide is subsequently separated from the water.

The processes described herein are not limited to particular reactor or coolant flow configurations, and those depicted in FIG. 1 are merely exemplary. For example, reactor 10 may include counter-current or co-current gaseous feed and coolant directions. Also, the sequence in which the various feed components (alkylene, oxygen, ballast gas, gaseous promoter) are introduced in process 20 and their respective points of introduction in process 20 may be varied from those shown in FIG. 1. An actual commercial alkylene oxide process may have different flow connections between the units 10, 40, and 50 shown in FIG. 1, and the depicted connections are merely exemplary.

If desired, recycle stream 18 may also be provided to minimize waste and increase savings as the recycling of unreacted reactants decreases the amount of fresh "make up" feed (e.g., fresh alkylene, oxygen, and ballast gas) supplied to reactor 10. One example of a suitable recycle system is depicted in FIG. 1. As shown in the figure, alkylene oxide absorber 40 produces an overhead gas stream comprising unreacted olefin, saturated hydrocarbon impurities or byproducts, and carbon dioxide. Carbon dioxide is removed in $CO_2$ removal unit 50 (e.g., a $CO_2$ scrubber) and exits $CO_2$ removal unit 50 in carbon dioxide stream 34. The overhead stream 19 from unit 50 is combined with $CO_2$ removal unit 50 bypass stream 46 to define recycle stream 18. Recycle stream 18 is combined with olefin feed 12, ballast gas 13, oxygen feed 15, and gas phase promoter feed 14 to define reactor feed stream 22. Purge line 32 is also provided to provide for the removal of saturated hydrocarbon impurities (e.g., ethane), inerts (such as argon), and/or byproducts (as well as carbon dioxide) to prevent their accumulation in reactor feed 22.

The olefin comprising olefin feed stream 12 may be any olefin, including aromatic olefins and di-olefins, whether conjugated or not. However, preferred olefins are mono-olefins having the following formula:

wherein, $R_1$ and $R_2$ are individually selected from the group consisting of hydrogen and alkyl radicals having from 1 to 6 carbon atoms. Propylene ($R_1$=$CH_3$, $R_2$=H) and ethylene ($R_1$=$R_2$=H) are more preferred, and ethylene is most preferred. Correspondingly, preferred alkylene oxides in reactor product stream 24 are of the formula:

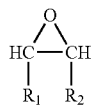

wherein, $R_1$ and $R_2$ are individually selected from the group consisting of hydrogen and alkyl radicals having from 1 to 6 carbon atoms. Propylene oxide ($R_1$=$CH_3$, $R_2$=H) and ethylene oxide ($R_1$=$R_2$=H) are more preferred, and ethylene oxide is most preferred.

Oxygen feed 15 may comprise substantially pure oxygen or air. If pure oxygen is used, ballast gases or diluents 13 such as nitrogen or methane may also be included to maintain the oxygen concentration below the maximum level allowed by flammability considerations. The concentration of oxygen in reactor feed stream 22 may vary over a wide range, and in practice, flammability is generally the limiting factor for oxygen concentration. Generally, the oxygen concentration in reactor feed 22 will be at least one (1) mole % and preferably at least two (2) mole %. The oxygen concentration will generally be no more than fifteen (15) mole %, preferably no more than twelve (12) mole %, and even more preferably no more than eight (8) mole %. The ballast gas 13 (e.g., nitrogen or methane) is generally from 50 mole % to 80 mole % of the total composition of reactor feed stream 22. Methane ballast gas is preferred over nitrogen because, due to its higher heat capacity, it facilitates the use of higher oxygen concentrations in the cycle, and therefore, improves both activity and efficiency.

The concentration of olefin in reactor feed stream 22 may vary over a wide range. However, it is preferably at least fifteen (15) mole % and more preferably at least twenty (20) mole %. The concentration of olefin in reactor feed stream 22 is preferably no greater than 50 mole %, and more preferably is no greater than 40 mole %.

When present, the carbon dioxide concentration in reactor feed stream 22 has a large adverse effect on the efficiency, activity and/or stability of catalysts used in reactor 10. Carbon dioxide is produced as a reaction by-product and may also be introduced with other inlet reaction gases as an impurity. In commercial ethylene epoxidation processes, at least part of the carbon dioxide is removed continuously in order to control its concentration to an acceptable level in the cycle. The carbon dioxide concentration in reactor feed 22 is generally no more than 5 mole %, preferably no more than 3 mole %, and even more preferably no more than 2 mole % of the total composition of reactor feed 22. Water is also a reaction by-product, and may be present in the feed gases in concentrations that are preferably from 0 to no more than three (3) mole %.

The gas phase promoter is generally a compound that enhances the efficiency and/or activity of process 20 for producing the desired alkylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred. Using chlorohydrocarbon gas phase promoters as an example, it is believed that the ability of the promoter to enhance the performance (e.g., efficiency and/or activity) of process 20 for the desired alkylene oxide depends on the extent to which the gas phase promoter chlorinates the surface of the catalyst in reactor 10, for example, by depositing particular chlorine species such as atomic chlorine or chloride ions on the catalyst or in the gas phase above the catalyst. However, hydrocarbons lacking chlorine atoms are believed to strip chlorides from the catalyst, and therefore, detract from the overall performance enhancement provided by the gas phase promoter. Discussions of this phenomenon may be found in Berty, "Inhibitor Action of Chlorinated Hydrocarbons in the Oxidation of Ethylene to Ethylene Oxide," *Chemical Engineering Communications*, Vol. 82 (1989) at 229-232 and Berry, "Ethylene Oxide Synthesis," *Applied Industrial Catalysis*, Vol. I (1983) at 207-238. Paraffinic compounds, such as ethane or propane, are believed to be especially effective at stripping chlorides from the catalyst. However, olefins such as ethylene and propylene are also believed to act to strip chlorides from the catalyst. Some of these hydrocarbons may also be introduced as impurities in the ethylene feed 12 or may be present for other reasons (such as the use of recycle stream 18). Typically, the preferred concentration of ethane in the reactor feed 22, when present, is from 0 to 2 mole %. Given the competing effects of the gas phase promoter and the non-halogenated, non-promoting hydrocarbons in reactor feed stream 22, it is convenient to define an "overall catalyst chloriding effectiveness value" that represents the net effect of gas phase species in chloriding the catalyst. In the case of organic chloride gas-phase promoters, the overall catalyst chloriding effectiveness can be defined as the dimensionless quantity Z* and represented by the following formula:

$$Z^* = \frac{\text{ethyl chloride equivalent}(ppmv)}{\text{ethane equivalent (mole \%)}} \quad (1)$$

wherein the ethyl chloride equivalent is the concentration in ppmv of ethyl chloride that provides substantially the same catalyst chloriding effectiveness of the organic chlorides present in reactor feed stream 22 at the concentrations of the organic chlorides in feed stream 22; and the ethane equivalent is the concentration of ethane in mole % that provides substantially the same catalyst dechloriding effectiveness of the non-chloride containing hydrocarbons in the reactor feed stream 22 at the concentrations of the non-chloride containing hydrocarbons in the reactor feed stream 22.

If ethyl chloride is the only gaseous chloride-containing promoter present in reactor feed stream 22, the ethyl chloride equivalent (i.e., the numerator in equation (1)) is the ethyl chloride concentration in ppmv. If other chlorine-containing promoters (specifically vinyl chloride, methyl chloride or ethylene dichloride) are used alone or in conjunction with ethyl chloride, the ethyl chloride equivalent is the concentration of ethyl chloride in ppmv plus the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed of 1 ppmv ethylene dichloride and 1 ppmv ethyl chloride, the ethyl chloride equivalent in the numerator of Z* would then be 3 ppmv. As a further example, it has been found that for certain catalysts methyl chloride has about one-tenth the chloriding effectiveness of ethyl chloride. Therefore, for such catalysts the ethyl chloride equivalent for a given concentration of methyl chloride in ppmv is 0.1× (methyl chloride concentration in ppmv). It has also been found that for certain catalysts, vinyl chloride has the same chloriding effectiveness as ethyl chloride. Therefore, for such catalysts the ethyl chloride equivalent for a given concentration of vinyl chloride in ppm is 1.0×(vinyl chloride concentration in ppmv). When more than two chlorine-containing promoters are present in reactor feed stream 22, which is often the case in commercial ethylene epoxidation processes, the overall ethyl chloride equivalent is the sum of the corresponding ethyl chloride equivalents for each individual chlorine-containing promoter that is present. As an example, for a hypothetical feed of 1 ppmv ethylene dichloride, 1 ppmv ethyl chloride, and 1 ppmv vinyl chloride, the ethyl chloride equivalent in the numerator of Z* would be 2*1+1+1*1=4 ppmv.

The ethane equivalent (i.e., the denominator in equation (1)) is the concentration of ethane in mole % in reactor feed stream 22 plus the concentration of the other hydrocarbons effective in removing chloride from the catalysts, corrected for their effectiveness for dechlorination relative to ethane. The relative effectiveness of ethylene compared to ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane. As a way of further illustration, if with a feed composition comprising an ethylene concentration of 30.0 mole % and an ethane concentration of 0.30 mole %, a level of 6.0 ppm ethyl chloride equivalents is found to provide the same level of catalyst performance as 3.0 ppm ethyl chloride equivalents with a similar feed composition but lacking ethane, then the ethane equivalent for 30.0 mole % ethylene would be 0.30 mole %. For an inlet reactor feed 22 having 30.0 mole % ethylene and 0.3 mole % ethane, the ethane equivalent will then be 0.6 mole %. As another illustration, it has been found that for certain catalysts methane has about one five-hundredth the dechloriding effectiveness of ethane. Thus, for such catalysts the ethane equivalent for methane is 0.002×(methane concentration in mol %). For a hypothetical inlet reactor feed 22 having 30.0 mole % ethylene and 0.1 mole % ethane, the ethane equivalent then will be 0.4 mole %. For an inlet reactor feed 22 having 30.0 mole % ethylene, 50 mole % methane, and 0.1 mole % ethane, the ethane equivalent then will be 0.5 mole %. The relative effectiveness of hydrocarbons other than ethane and ethylene can be measured experimentally by determining the inlet ethyl chloride equivalent concentrations required to achieve the same catalyst performance for a feed comprising the hydrocarbon of interest at its concentration in the feed at two different concentrations of ethane in the feed. If a hydrocarbon compound is found to have a very small dechloriding effect and is also present in low concentrations, then its contribution to the ethane equivalent concentration in the Z* calculation may be negligible.

Thus, given the foregoing relationships, in the case where reactor feed stream 22 includes ethylene, ethyl chloride, ethylene dichloride, vinyl chloride, ethane, and no methane the overall catalyst chloriding effectiveness value of process 20 can be defined as follows:

$$Z^* = \frac{(ECL + 2^*EDC + VCL)}{(C_2H_6 + 0.01^*C_2H_4)} \quad (2)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C=CH$—Cl), respectively, in reactor feed stream 22. $C_2H_6$ and $C_2H_4$ are the concentrations in mole % of ethane and ethylene, respectively, in reactor feed stream 22. It is important that the relative effectiveness of the gaseous chlorine-containing promoter and the hydrocarbon dechlorinating species also be measured under the reaction conditions which are being used in the process. Z* will preferably be maintained at a level that is no greater than 20 and which is most preferably no greater than 15. Z* is preferably at least 1.

Although the gaseous chlorine-containing promoter may be supplied as a single species, upon contact with the catalyst, other species may be formed leading to a mixture in the gas phase. Consequently, if the reaction gases are recycled such as via recycle stream 18, a mixture of species will be found in the inlet of the reactor. In particular, the recycled reaction gases at the inlet may contain ethyl chloride, vinyl chloride, ethylene dichloride and methyl chloride, even though only ethyl chloride or ethylene dichloride is supplied to the system. The concentrations of ethyl chloride, vinyl chloride, methyl chloride and ethylene dichloride must be considered in calculating Z*.

The order in which the inlet gases (alkylene oxide and oxygen and ballast gas) and gas phase promoter are mixed together is not critical, and they may be mixed simultaneously or sequentially. The order of mixing of the gaseous components of the process may be chosen for convenience and/or for safety reasons. For example, oxygen is generally added after the ballast gas for reasons of safety. However, the gas phase promoter should be present in reactor feed stream 22 as it is introduced to the solid catalyst in reactor 10.

In the embodiment of FIG. 1, Reactor 10 is a fixed bed reactor. However, any suitable reactor may be used, for example, fixed bed tubular reactors, continuous stirred tank reactors (CSTR), and fluid bed reactors, a wide variety of which are well known to those skilled in the art and need not be described in detail herein. The desirability of recycling unreacted feed, or employing a single-pass system, or using successive reactions to increase ethylene conversion by employing reactors in series arrangement can also be readily determined by those skilled in the art. The particular mode of operation selected is usually dictated by process economics. The epoxidation reaction is generally exothermic. Thus, a coolant system 28 (e.g., a cooling jacket or a hydraulic circuit with a coolant fluid such as a heat transfer fluid or boiling water) is provided to regulate the temperature of reactor 10. The heat transfer fluid can be any of several well-known heat transfer fluids, such as tetralin (1,2,3,4-Tetrahydronaphthalene). In reactors cooled with boiling water, the coolant is introduced to the cooling side of the reactor, most commonly the shell side, as liquid water. As it flows through the cooling side, the water removes heat from the process side, and some of the water is vaporized to steam. The coolant exits the cooling side of the reactor as a mixture of water and steam. The steam exiting the reactor is condensed by removing heat from it, and is recycled back to the inlet of the coolant side. The temperature of the coolant in the reactor is determined by the boiling point of the water, which in turn is determined by the pressure under which it operates. The pressure is controlled by means of a vent valve which vents off some pressure from the steam-water mixture exiting the cooling side of the reactor. Typically, a closed-loop controller is used to regulate the coolant temperature by automatically adjusting the vent valve to maintain the pressure necessary to maintain the desired temperature. The epoxidation reaction is carried out at a temperature that is preferably at least 200° C., more preferably at least 210° C., and most preferably at least 220° C. Reactor temperatures of no more than 300° C. are preferred, and reactor temperatures of no more than 290° C. are more preferred. Reactor temperatures of no more than 280° C. are most preferred. The reactor pressure is selected based on the desired mass velocity and productivity and ranges generally from 5 atm (506 kPa) to 30 atm (3.0 MPa). The gas hourly space velocity (GHSV) is preferably greater than 3000 $h^{-1}$, more preferably greater than 4,000 $h^{-1}$, and most preferably greater than 5,000 $h^{-1}$.

Reactor 10 includes a high efficiency, silver catalyst. Generally, the highly efficient silver based catalyst is a supported catalyst. The support (also known as a "carrier") may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is α-alumina. In one exemplary embodiment, silver is deposited on the catalyst carrier as are one or more solid promoters, which are discussed further below.

There are many well-known methods of preparing supports suitable for use in ethylene oxide catalysts. Some of such methods are described in, for example, U.S. Pat. Nos. 4,379, 134; 4,806,518; 5,063,195; 5,384,302, U.S. Patent Application 20030162655 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives. Another method for preparing a carrier having particularly suitable properties for ethylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina carrier.

There have been employed alumina which has a very high purity, that is, at least 98 wt. % alpha-alumina, any remaining components being silica, alkali metal oxides (for example, sodium oxide) and trace amounts of other metal-containing and/or non-metal-containing additives or impurities. Likewise, there have been employed alumina of lower purity, that is, 80 wt. % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the carrier may comprise compounds which have been known for improving catalyst performance, for example, rhenium, (such as rhenates) and molybdenum.

In an especially preferred embodiment, the support material comprises at least 80 weight percent α-alumina and less than 30 parts per million acid-leachable alkali metals by weight, the weight percent of the α-alumina and the concentration of the acid-leachable alkali metals being calculated on the weight of the carrier, where the acid-leachable alkali metals are selected from lithium, sodium, potassium, and mixtures thereof.

The alpha-alumina carrier prepared as described hereinabove preferably has a specific surface area of at least 0.5 $m^2/g$, and more preferably, at least 0.7 $m^2/g$. The surface area is typically less than 10 $m^2/g$, and preferably, less than 5 $m^2/g$. The alpha-alumina carrier preferably has a pore volume of at least 0.3 $cm^3/g$, and more preferably, from 0.4 $cm^3/g$ to 1.0 $cm^3/g$ and a median pore diameter from 1 to 50 microns. A variety of carrier morphologies may be used, including pills, cylinders, cylinders with one or more longitudinal axial openings, chunks, tablets, pieces, pellets, rings, spheres, wagon wheels, saddle rings and toroids having star shaped inner and/or outer surfaces. In a preferred embodiment, the high-purity alpha-alumina preferably includes particles many of which have at least one substantially flat major surface, and having a lamellate or platelet morphology. In a more preferred embodiment the particles approximate the shape of a hexagonal plate (some particles having two or more flat surfaces), at least 50 percent of which (by number) have a major dimension of less than 50 microns. In a preferred embodiment, the alpha-alumina carrier comprises zirconium silicate (zircon), present substantially as zirconium silicate in the finished carrier, more preferably, in an amount up to 4 weight percent, calculated on the weight of the carrier.

Catalysts of this invention for the production of alkylene oxide, for example, ethylene oxide or propylene oxide may be prepared with the aforementioned carriers by impregnating the carrier with a solution of one or more silver compounds, depositing the silver throughout the pores of the carrier and reducing the silver compound as is well known in the art. See for example, Liu, et al., U.S. Pat. No. 6,511,938 and Thorsteinson et al., U.S. Pat. No. 5,187,140.

Generally, the carrier is impregnated with a catalytic amount of silver, which is any amount of silver capable of catalyzing the direct oxidation of the alkylene with oxygen or an oxygen-containing gas to the corresponding alkylene oxide. In making such a catalyst, the carrier is typically impregnated (one or more times) with one or more silver compound solutions sufficient to allow the silver to be supported on the carrier in an amount greater than 5 percent, greater than 10 percent, greater than 15 percent, greater than 20 percent, greater than 25 percent, preferably, greater than 27 percent, and more preferably, greater than 30 percent by weight, based on the weight of the catalyst. Typically, the amount of silver supported on the carrier is less than 70 percent, and more preferably, less than 50 percent by weight, based on the weight of the catalyst.

Although silver particle size in the finished catalyst is important, the range is not narrow. A suitable silver particle size can be in the range of from 10 to 10,000 angstroms in diameter. A preferred silver particle size ranges from greater than 100 to less than 5,000 angstroms in diameter. It is desirable that the silver be relatively uniformly dispersed within, throughout, and/or on the alumina carrier.

As is known to those skilled in the art, there are a variety of known promoters, that is, materials which, when present in combination with particular catalytic materials, for example, silver, benefit one or more aspects of catalyst performance or otherwise act to promote the catalyst's ability to make a desired product, for example ethylene oxide or propylene oxide. Such promoters in themselves are generally not considered catalytic materials. The presence of such promoters in the catalyst has been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, for example ethylene oxide. The concentration of the one or more promoters present in the catalyst may vary over a wide range depending on the desired effect on catalyst performance, the other components of a particular catalyst, the physical and chemical characteristics of the carrier, and the epoxidation reaction conditions.

There are at least two types of promoters—solid promoters and gaseous promoters. The solid and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst.

The presence of other activators, stabilizers, promoters, enhancers or other catalyst improvers can also affect the promoting effects.

Examples of well-known solid promoters for catalysts used to produce ethylene oxide include compounds of potassium, rubidium, cesium, rhenium, sulfur, manganese, molybdenum, and tungsten. During the reaction to make ethylene oxide, the specific form of the promoter on the catalyst may be unknown. Examples of solid promoter compositions and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261. The solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. For the sake of ease of understanding, the solid promoters will be referred to in terms of cations and anions regardless of their form in the catalyst under reaction conditions.

The catalyst prepared on the carrier may contain alkali metal and/or alkaline earth metal as cation promoters. Exemplary of the alkali metal and/or alkaline earth metals are lithium, sodium, potassium, rubidium, cesium, beryllium, magnesium, calcium, strontium and barium. Other cation promoters include Group 3b metal ions including lanthanide series metals. In some instances, the promoter comprises a mixture of cations, for example cesium and at least one other alkali metal, to obtain a synergistic efficiency enhancement as described in U.S. Pat. No. 4,916,243. Note that references to the Periodic Table herein shall be to that as published by the Chemical Rubber Company, Cleveland, Ohio, in CRC Handbook of Chemistry and Physics, 46th Edition, inside back cover.

The concentration of the alkali metal promoters in the finished catalyst is not narrow and may vary over a wide range. The optimum alkali metal promoter concentration for a particular catalyst will be dependent upon performance characteristics, such as catalyst efficiency, rate of catalyst aging and reaction temperature.

The concentration of alkali metal (based on the weight of cation, for example cesium) in the finished catalyst may vary from 0.0005 to 1.0 wt. %, preferably from 0.005 to 0.5 wt. %. The preferred amount of cation promoter deposited on or present on the surface of the carrier or catalyst generally lies between 10 and 4000, preferably 15 and 3000, and more preferably between 20 and 2500 ppm by weight of cation calculated on the total carrier material. Cation promoter amounts between 50 and 2000 ppm by weight of the total carrier material are frequently most preferable. When the alkali metal cesium cation is used in mixture with other cations, the ratio of cesium to any other alkali metal and alkaline earth metal cation(s), if used, to achieve desired performance is not narrow and may vary over a wide range. The weight ratio of cesium to the other cation promoters may vary from 0.0001:1 to 10,000:1, preferably from 0.001:1 to 1,000:1.

Examples of some of the anion promoters which may be employed with the present invention include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications.

The types of anion promoters or modifiers suitable for use in the catalysts of this invention comprise, by way of example only, oxyanions such as sulfate, $[SO_4]^{-2}$, phosphates, for example, $[PO_4]^{-3}$, titanates, e.g., $[TiO_3]^{-2}$, tantalates, for example, $[Ta_2O_6]^{-2}$, molybdates, for example, $[MoO_4]^{-2}$, vanadates, for example, $[V_2O_4]^{-2}$, chromates, for example, $[CrO_4]^{-2}$, zirconates, for example, $[ZrO_3]^{-2}$, polyphosphates, manganates, nitrates, chlorates, bromates, borates, silicates, carbonates, tungstates, thiosulfates, cerates and the like. The halides may also be present, including fluoride, chloride, bromide and iodide.

It is well recognized that many anions have complex chemistries and may exist in one or more forms, for example, orthovanadate and metavanadate; and the various molybdate oxyanions such as $[MoO_4]^{-2}$, and $[Mo_7O_{24}]^{-6}$ and $[Mo_2O_7]^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

With certain highly efficient catalysts, the most preferred promoter comprises rhenium, which can be provided in various forms, for example, as the metal, as a covalent compound, as a cation or as an anion (including, without limitation, an oxyanion). The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Another class of promoters, which may be employed with the present invention, includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylene-diamine-tetraacetic acid (EDTA) or a suitable salt thereof.

The amount of anion promoter may vary widely, for example, from 0.0005 to 2 wt. %, preferably from 0.001 to 0.5 wt. % based on the total weight of the catalyst. When used, the rhenium component is often provided in an amount of at least 1, say, at least 5, for example, 10 to 2000, often between 20 and 1000, ppmw calculated as the weight of rhenium based on the total weight of the catalyst.

It is desirable that the silver and one or more solid promoters be relatively uniformly dispersed on the carrier. Well known methods can be employed to analyze for the amounts of silver and solid promoters deposited onto the alumina carrier. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

Figure 2:
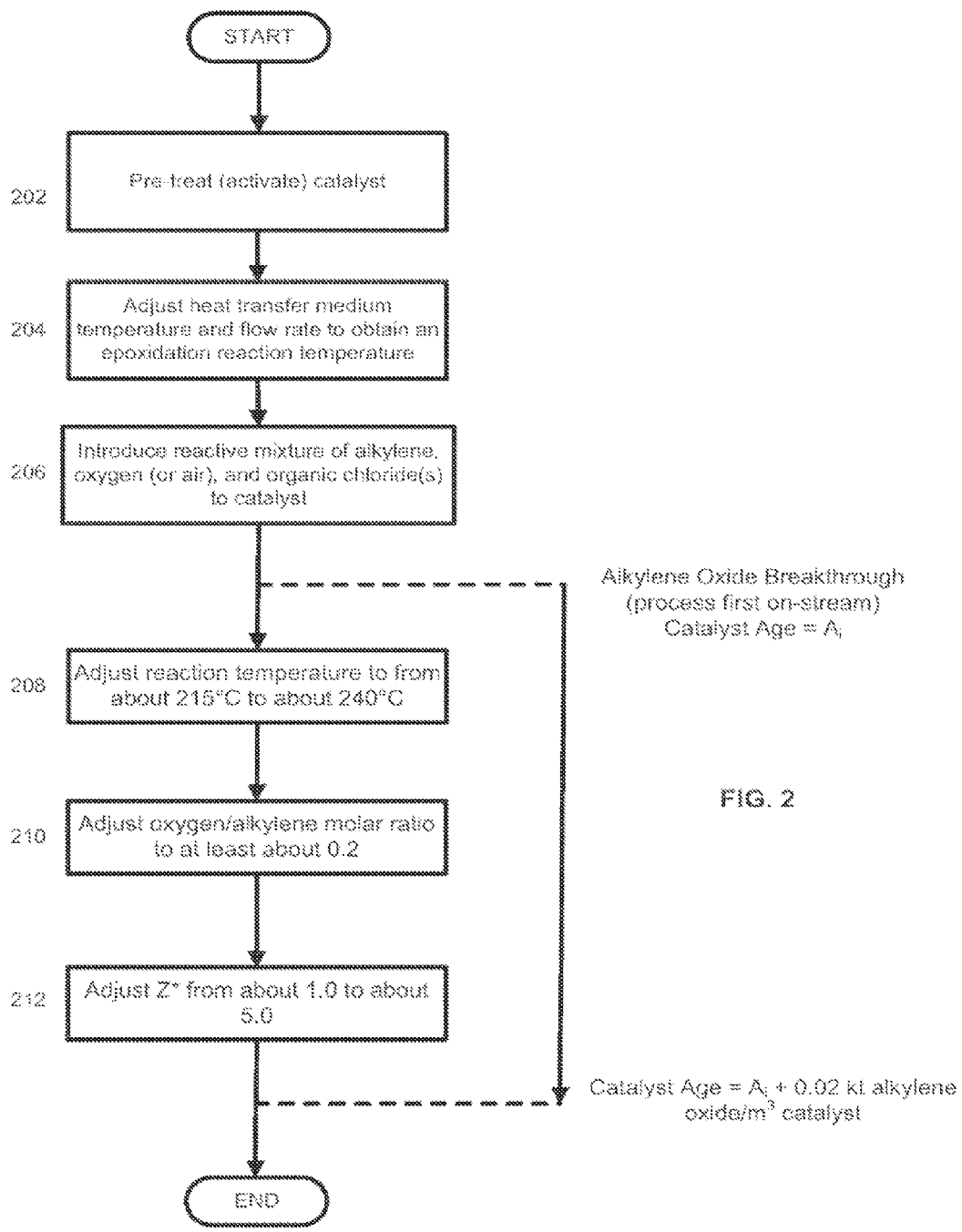
FIG. 2 is flow chart depicting an embodiment of a method of starting-up a high efficiency alkylene oxide catalyst.

As mentioned previously, it has been found that the selection of start-up conditions can have a significant effect on the performance of high efficiency silver catalysts of the type described herein. A method of starting-up a fresh or aged high efficiency silver catalyst used in the production of an alkylene oxide is depicted in FIG. 2. Prior to start-up, the catalyst is not subjected to a reactive combination of alkylene and oxygen and produces no alkylene oxide. In certain preferred methods, the catalyst is first pre-treated (step 202) to enhance its activity. Any known pre-treatment method may be used in step 202. Typical methods include subjecting the catalyst to one or more inert gases (e.g., nitrogen, methane, and/or alkylene) at a selected temperature, temperatures, or temperature range for a period of time.

In step 204, the catalyst in reactor 10 is brought up to an epoxidation reaction temperature (i.e., a temperature sufficient to initiate an epoxidation reaction) by adjusting the flow and/or temperature of the heat transfer medium in coolant circuit 28. Because epoxidation has not yet begun, the heat transfer medium will transfer heat to the catalyst and must be at a temperature higher than the desired reaction temperature. It should be noted that the terms "reaction temperature," "epoxidation temperature" or "epoxidation reaction temperature" refer to any selected temperature(s) that are directly or indirectly indicative of the catalyst bed temperature. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor inlet coolant temperature or outlet temperature. The epoxidation temperature in step 204 will generally be at least 150° C.

In step 206, the catalyst in reactor 10 is subjected to a reactive mixture of an alkylene, oxygen, and at least one organic chloride. In step 208, the reaction temperature is adjusted to within the range of generally from 215° C. to 240° C., and more preferably from 225° C. to 235° C.

In step 210, the molar ratio of oxygen to alkylene is adjusted to a value of at least 0.2. The ratio may be adjusted in a number of ways. In one example, the oxygen feed rate 15 (or air in air-based processes) is increased while holding the alkylene feed rate 12 constant. In another example, the alkylene feed rate 12 is decreased while holding the oxygen feed rate 15 constant. In another example, both oxygen and alkylene feed rates 15, 12 are increased, with oxygen being increased to a greater extent than alkylene. In further examples, the oxygen feed rate 15 is increased and the alkylene feed rate 12 is decreased. In certain embodiments, the ratio of oxygen to alkylene is adjusted to a value no greater than 0.35.

In step 212, the overall catalyst chloriding value, $Z^*$, is adjusted to a value that is preferably from 1.0 to 5.0, more preferably from 1.0 to 3.5, and still more preferably from between 1.0 to 2.5. $Z^*$ may be adjusted by adjusting the at least one organic chloride feed rate 14, the alkylene feed rate 12, and/or the recycle rate 18.

Steps 208, 210, and 212 are preferably accomplished within a fixed catalyst aging period after reactor 10 is first on-stream. The upper most horizontal dashed line in FIG. 2 represents the point when alkylene oxide is first produced, and therefore, when reactor 10 is first on-stream. In certain examples, the first measurement of alkylene oxide in net product stream 16 is used to determine when reactor 10 is first on stream. Steps 208, 210, and 212 are preferably accomplished within a catalyst aging period of 0.03 kT alkylene oxide/m³ catalyst, more preferably no later than when the catalyst age is 0.02 kt alkylene oxide/m³ catalyst, and even more preferably no later than 0.018 kT alkylene oxide/m³ catalyst, after the process is first on-stream. In addition, in certain preferred embodiments, step 210 is carried out such that within a period of no more than 5 hours after the process is first on-stream, the molar ratio of oxygen to alkylene is at least 0.15.

In FIG. 2, the adjustments to reaction temperature, oxygen/alkylene molar ratio, and $Z^*$ are depicted as occurring after reactor 10 is first on-stream. However, any or all of the adjustment of reaction temperature, oxygen/alkylene molar ratio, and $Z^*$ in steps 208, 210, and 212 may be accomplished prior to the point when reactor 10 first goes on stream. In addition, steps 208, 210, and 212 may be performed in any relative order. The sequence shown in FIG. 2 is merely exemplary. Each of the steps may also be carried out in a variety of ways, including without limitation, step changes, ramp changes, non-linear changes, and combinations of each.

In certain preferred embodiments, after completing steps 208, 210, and 212, the start-up process continues and further process adjustments are made to achieve a desired value of a target alkylene oxide production parameter, such as the concentration of alkylene oxide in the reaction product. Start-up is generally considered to be complete once the alkylene oxide production parameter has reached the target value and fluctuates from the target value by no more than 5 percent, preferably no more than 3 percent, more preferably no more than 2 percent, and even more preferably no more than 1 percent from the target value. In certain embodiments, the adjustments to the molar ratio of oxygen to alkylene are made no longer than until the alkylene oxide production parameter is substantially equal to the target value. In other embodiments, the adjustments to the molar ratio of oxygen to alkylene are made no longer than until the alkylene oxide production parameter fluctuates by no more than a pre-selected amount. In further embodiments, adjustments to the molar ratio are made no longer than 10 days, preferably no longer than 7 days, and more preferably no longer than 5 days after the process is first on-stream.

In certain examples, once it is at least 0.2, the molar ratio of oxygen to alkylene is further increased to drive the alkylene oxide production parameter toward the target value. However, the ratio is preferably adjusted no longer than until the alkylene oxide production parameter reaches the target value of the alkylene oxide production parameter. In other examples, the ratio is increased no longer than until the alkylene oxide production parameter fluctuates by no more than a pre-selected amount. In certain embodiments, the pre-selected amount is 5 percent of the target value, preferably 3 percent of the target value, more preferably 2 percent of the target value, and even more preferably 1 percent of the target value. In embodiments wherein the target alkylene oxide production parameter is the concentration of the alkylene oxide in the reaction product, the target value is preferably at least 0.5 mole %, more preferably at least 0.8 mole %, still more preferably at least 1.0 mole % and even more preferably at least 1.5 mole % alkylene oxide.

In other embodiments, the adjustments to the molar ratio of oxygen to alkylene are carried out until the efficiency of the process to the alkylene oxide is at least 85 percent, preferably at least 87 percent, more preferably at least 88 percent.

Unless accompanied by an increase in ballast feed 13, increasing the oxygen to alkylene ratio in step 210 will increase the concentration of oxygen in the reactor feed 22. The oxygen concentration will generally be no more than fifteen (15) mole %, preferably no more than twelve (12) mole %, and even more preferably no more than nine (9) mole %. The ballast gas 13 (e.g., nitrogen or methane) is generally from 50 mole % to 80 mole % of the total composition of reactor feed stream 22. Methane ballast gas is preferred over nitrogen because, due to its higher heat capacity, it facilitates the use of higher oxygen concentrations in the cycle, and therefore, improves both activity and efficiency.

In certain embodiments, a pre-selected maximum oxygen concentration is selected which is no greater than an amount of oxygen that would form a flammable mixture with the components of reactor feed 22 at the prevailing process conditions (the "oxygen flammability concentration"). In other embodiments, the maximum oxygen concentration is no greater than a pre-defined percentage of the oxygen flammability concentration (e.g., the maximum oxygen concentration is no greater than 95% of the oxygen flammability concentration and preferably no greater than 90% of the oxygen flammability concentration). In certain further embodiments, the maximum oxygen concentration and/or the oxygen flammability concentration is determined based on at least one variable selected from the group consisting of reaction temperature, pressure, alkylene concentration, alkylene oxide concentration, ballast gas concentration, and carbon dioxide concentration in reactor feed 22.

Following the completion of step 208, further adjustments to reaction temperature may be made to increase an alkylene oxide production parameter to a selected target value. However, the reaction temperatures resulting from such further adjustments are preferably from 215° C. to 240° C. and more preferably from 225° C. to 235° C. Similarly, following the completion of step 212 further adjustments to overall chloriding catalyst effectiveness may be made to increase an alkylene oxide production parameter to a selected target value. However, the values of Z* resulting from such adjustments are preferably from 1.0 to 5.0, more preferably from 1.0 to 3.5, and more preferably from 1.0 to 2.5. As mentioned previously, the efficiency to alkylene oxide of high efficiency catalysts of the type described herein may be sensitive to changes in either reaction temperature or overall catalyst chloriding effectiveness. Thus, in certain preferred embodiments, coordinated adjustments are made to both temperature and overall catalyst chloriding effectiveness to affect the desired changes in the alkylene oxide production parameter. In one embodiment, the coolant temperature is used as an indication of reaction temperature, and the coolant temperature and overall catalyst chloriding effectiveness are adjusted in accordance with the following relationship:

$$Z^* = (T_{rx} - T_o)/S_o \qquad (6)$$

wherein, $T_{rx}$ is the reactor coolant inlet temperature in ° C.,
$T_o$ is the temperature-axis intercept of equation (6) which is determined by extrapolating a plot of Z* versus $T_{rx}$ to Z*=0, and
$S_o$ is a slope relating the change in inlet coolant temperature to the corresponding change in Z*.

The effectiveness of the foregoing relationship generally depends on the value of the temperature-axis intercept $T_o$ and the slope $S_o$. The values of $T_0$ for which the foregoing equation is suitable are preferably from 205° C. to 220° C., more preferably from 208° C. to 218° C., and even more preferably from 211° C. to 217° C. The reaction temperatures resulting from such further adjustments are preferably from 215° C. to 240° C. and more preferably from 225° C. to 235° C. Preferred values of slope $S_o$ range from 5 to 8. Slope values of from 5.5 to 7.5 are more preferred, and values of from 6.0 to 6.5 are still more preferred. A slope of 6.25 is especially preferred.

It has also been discovered that the variable adjustments of FIG. 2 can advantageously be used to revive an underperforming catalyst without the need for a shutdown. In accordance with the method, at least one process parameter is adjusted to increase the efficiency of the process to the alkylene oxide. The at least one process parameter is selected from the group consisting of the molar ratio of oxygen to alkylene, reaction temperature, and Z*. Following the adjustment step, the molar ratio of oxygen to alkylene is at least 0.2 (and preferably at least 0.2), the reaction temperature is from 215° C. to 240° C., and Z* is from 1.0 to 5.0. In a preferred embodiment, Z* is from 1.0 to 3.5 following the adjusting step. In a more preferred embodiment, Z* is from 1.0 to 2.5 following the adjusting step. In a preferred embodiment, the reaction temperature is from 225° C. to 235° C. following the adjusting step. In a further preferred embodiment, Z* is from 1.0 to 2.5 and the reaction temperature is from 225° C. to 235° C. following the adjusting step. In certain exemplary embodiments, the adjustment step comprises adjusting the reaction temperature from a value outside of the range of from 215° C. to 240° C. to a value inside that range, and preferably comprises adjusting the reaction temperature from a value outside of the range of from 225° C. to 235° C. to a value inside the range of from 225° C. to 235° C.

In other exemplary embodiments, the adjustment step comprises adjusting Z* from a value outside of the range of from 1.0 to 5.0 to a value inside that range and preferably comprises adjusting Z* from a value outside of the range of from 1.0 to 3.5 to a value inside the range of from 1.0 to 3.5. In additional embodiments, the adjustment step comprises adjusting Z* from a value outside of the range of from 1.0 to 2.5 to a value inside the range of from 1.0 to 2.5.

In further exemplary embodiments the adjustment step comprises adjusting the molar ratio of oxygen to ethylene from a value less than 0.2 to a value greater than 0.2, and more preferably comprises adjusting the molar ratio of oxygen to ethylene from a value less than 0.2 to a value ranging from 0.2 to 0.35.

Figure 3:
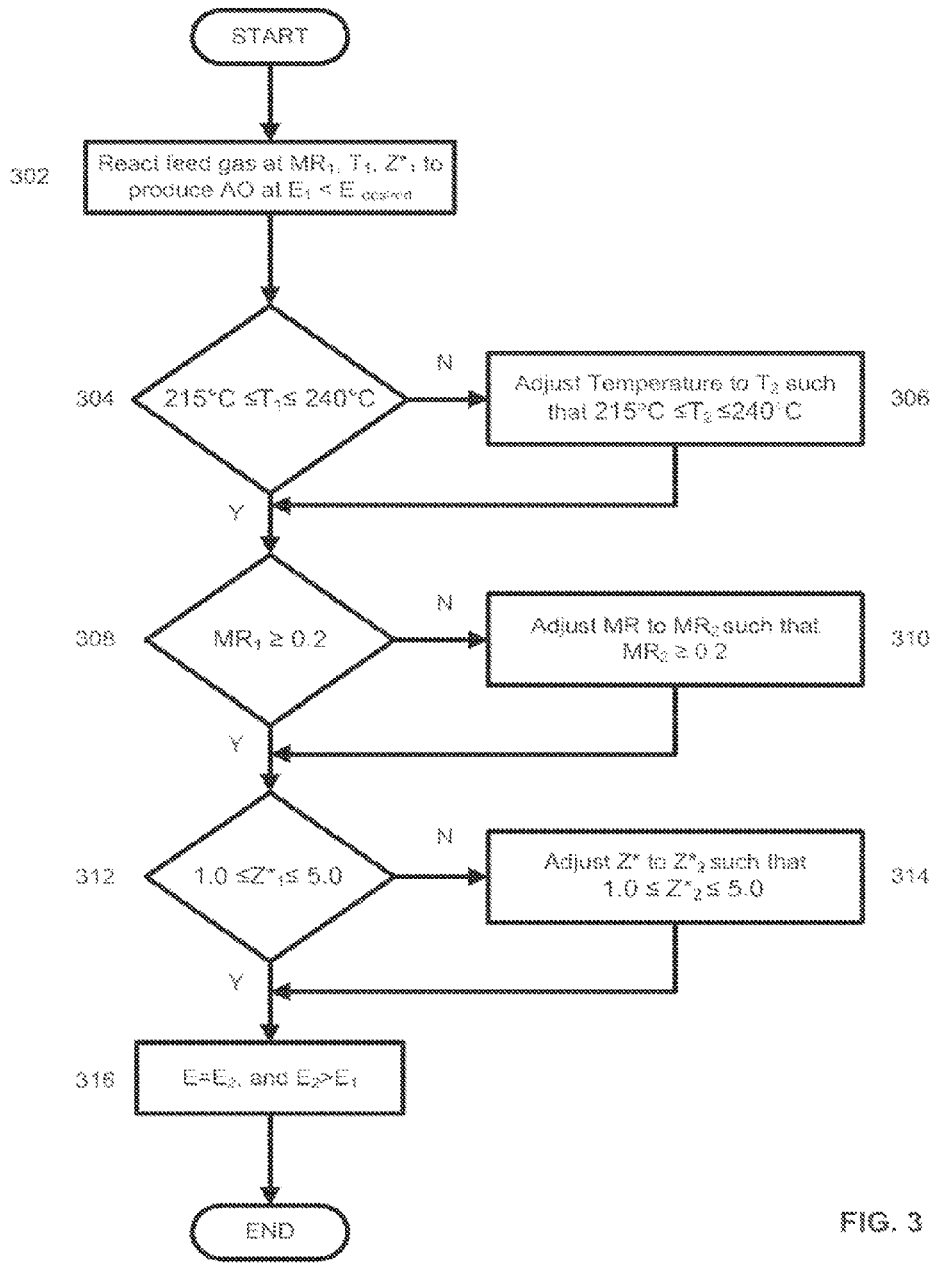
FIG. 3 is a flow chart depicting an embodiment of a method of reviving the performance of a high efficiency alkylene oxide catalyst.

Referring to FIG. 3, a method of reviving a high efficiency catalyst used in the production of an alkylene oxide (AO) is depicted. In accordance with the method, process 20 is operated at step 302 by reacting feed 22 at a first molar ratio of oxygen to alkylene, a first reaction temperature ($T_1$), and a first overall chloriding effectiveness, $Z^*_1$, to produce an alkylene oxide. In step 302 the observed efficiency to the alkylene oxide, $E_1$, is less than a desired or target efficiency, $E_{desired}$. In step 304, a determination is made as to whether the reaction temperature is in the range of from 215° C. to 240° C. If the temperature is in the range, the method proceeds to step 308. Otherwise, the temperature is adjusted to $T_2$, wherein $T_2$ is in the range from 215° C. to 240° C. In certain preferred implementations, if the reaction temperature is not within the range of from 225° C. to 235° C., it is adjusted to a value within that range in step 304. In other preferred implementations, during step 304 it is further determined whether the first reaction temperature $T_1$ and the first overall chloriding effectiveness $Z^*_1$ follow the relationship of Equation (6), above. If they do not, then in step 304 the reaction temperature is adjusted to a second reaction temperature $T_2$ based on the first overall chloriding effectiveness $Z^*_1$ and the relationship of Equation (6).

In step 308, it is determined whether the initial molar ratio of oxygen to alkylene ($MR_1$) is at least 0.2. If the ratio is at least 0.2, the method proceeds to step 312. Otherwise, the molar ratio is adjusted to at least 0.2. In step 310, the molar ratio of oxygen to alkylene is preferably adjusted to no more than 0.35. In certain preferred implementations of step 308, if the molar ratio of oxygen to alkylene is not at least 0.3, it is adjusted to at least that value. In certain embodiments of step 308, the molar ratio is adjusted to a first value of at least 0.2 and a second value of at least 0.2, wherein the second value is greater than the first.

In step 312, it is determined whether $Z^*$ is from 1.0 to 5.0. If $Z^*$ is in this range, no action is taken and the process efficiency adjusts to $E_2$ in step 316. Otherwise, $Z^*$ is adjusted to a value from 1.0 to 5.0. In certain preferred implementations of step 312, if $Z^*$ is not in the range of from 1.0 to 3.5, it is adjusted to lie within that range. In certain further preferred implementations of step 312, if $Z^*$ is not in the range of from 1.0 to 2.5, it is adjusted to lie within that range. In other preferred implementations, $Z^*$ is adjusted to a second value in accordance with the relationship of Equation (6). Steps 306, 310, and 314 may be carried out in a number of different sequences and ways, including step changes, ramp changes, non-linear changes, and combinations of each.

EXAMPLES

The following examples illustrate the effects of various embodiments of the start-up and catalyst revival methods described herein. In several of the examples, the reaction product is characterized by the alkylene (in this case, ethylene) oxide production parameter "delta EO" also referred to as "dEO" or "ΔEO." For a given reactor inlet concentration of ethylene oxide, $EO_{Inlet}$, and reaction product concentration of ethylene oxide, $EO_1$, the parameter ΔEO is related to the concentration of ethylene oxide in the reaction product as follows:

$$\text{Shrink Factor (SF)} = (200 + C_{EO\,Inlet})/(200 + C_{EO1}). \quad (7)$$

$$\Delta EO\,\% = SF \cdot C_{EO1} - C_{EO\,Inlet} \quad (8)$$

The "Shrink Factor" represents the net volumetric reduction occurring due to the production of the alkylene oxide. For example, in the case of ethylene oxide production, for every mole of ethylene oxide produced, there is a net reduction of 0.5 moles of total gas resulting in a corresponding reduction in the volumetric flow rate.

Example 1

At start up a feed gas comprising 20 mole % ethylene, 0.3 mole % ethane, 5 mole % oxygen, 0.9 mole % $CO_2$, 1.1 ppmv ethyl chloride, and the balance nitrogen is introduced to a high efficiency, rhenium-promoted silver catalyst loaded in a pilot plant reactor and is put on stream for 45 days. The pilot plant reactor tubes have a volume of 0.113 ft³. At start-up, the molar ratio of oxygen to ethylene is 0.25. The start-up inlet coolant temperature (ICT) is 227° C., and the start-up $Z^*$ is 2.2. By day 3 on stream (0.6 klb/ft³ (0.010 kT/m³) cumulative ethylene oxide production) the oxygen concentration is raised to 5.5 mole %, the ethylene concentration is raised to 35 mole %, the ethane concentration is raised to 0.6 mole %, the $CO_2$ concentration is raised to 1.5 mole %, and the ethyl chloride concentration is raised to 1.8 ppmv. The ICT is raised to 231° C. This temperature and the oxygen to ethylene molar ratio of 0.158 are maintained until day 7 on stream (1.9 klb/ft³ (0.030 kT/m³) cumulative EO production). At day 8 on stream (2.3 klb/ft³ (0.037 kT/m³) cumulative EO production), the oxygen concentration is raised to 8.2 mole %, and the ethylene concentration is adjusted to 30 mole %. The ethane concentration remains at 0.6 mole %, and the $CO_2$ concentration is adjusted to 1.6 mole %. The resulting oxygen to ethylene molar ratio is 0.27. Also at day 8 on stream, the ICT is adjusted to between 225-235° C. to maintain dEO at 2.2 mole %, and $Z^*$ is adjusted to achieve the best possible efficiency at the ICT using Equation (6), above.

The results of Example 1 are provided in FIGS. 4A-4B. As FIG. 4A indicates, the molar ratio is dropped to 0.2 on days 2 and 3 and to 0.15-0.16 between days 3.5 and 8. The efficiency to ethylene oxide which is 89.7% drops steadily to 85.4% by day 8 on stream. On day 9, the molar ratio of oxygen to ethylene is increased to 0.27. After 40 days on stream (13.6 klb/ft³ (0.218 kT/m³) cumulative EO production) with the molar ratio at 0.27, the efficiency increases to 87.5%. Temperature is raised to 232° C. between days 4-9 and dropped to 222° C. by day 20. After day 20, the temperature is steadily increased to 230° C. by day 38. $Z^*$ is held at 2.2 until day 8 and is then dropped to 1.4 by day 10. After day 10, $Z^*$ is increased to 2.6 by day 15 on stream and further increased to 3.0 by day 41. The run is conducted at a 2.2% Δ EO. Throughout the run, the pressure is 290 psig and the total gas flow rate is 595 scfh. Trends of Δ EO, $Z^*$ and ICT are shown in FIG. 4B. Thus, FIGS. 4A-B illustrate the detrimental effect of lowering the molar ratio of oxygen to ethylene below 0.20 during start-up.

Example 2 (Comparative)

A feed gas comprising ethylene, oxygen, and ethyl chloride is fed to a high efficiency, rhenium-promoted silver catalyst loaded in a pilot plant reactor with a tube volume of 0.0866 ft³. The reactor pressure is 295 psig, and the total feed gas flow rate is 435 scfh. Feed composition at start of run on day 1 is 5 mole % oxygen, 0.3 mole % $CO_2$, 16 mole % ethylene, 0.6 mole % ethane, and 1.64 ppmv ECl. The start of run molar ratio of oxygen to ethylene is 0.3. The initial start-up temperature is 220° C., and the temperature is subsequently maintained at 215° C. throughout the run. $Z^*$ is typically 1.6-1.7 throughout the run. By day 3 on stream, the oxygen to ethylene molar ratio is decreased to 0.16, and by day 6 on stream the ratio is further decreased to 0.14 by increasing the concentration of ethylene in the feed. $Z^*$ and temperature values are shown in FIG. 5B. Δ EO is typically 1.63% throughout the run. Later in the run, the feed composition is 35 mole % ethylene, 0.6 mole % ethane, 5 mole % oxygen, and 0.6 mole % $CO_2$, with the ECL concentration typically ranging from 1.4-1.5 ppmv and the balance being nitrogen.

As shown in FIG. 5A, the start of run efficiency is 87.8% and increases to 89% by day 2. On day 2, the molar ratio of oxygen to ethylene is decreased to 0.2. The molar ratio is then decreased to 0.17 on day 3 and to 0.15 on day 6, and the efficiency drops to 86 mole %. The reactor trips on days 6, 12, and 20. Typically, recovery after a reactor trip yields some benefit in efficiency. However, following the trip on day 6, the efficiency drops to 84.6%. Following each trip, selectivity shows some attempt to improve but drops back down, which is believed to be attributable to the low molar ratio of oxygen to ethylene.

Example 3

A feed gas comprising 27 mole % ethylene, 0.6 mole % ethane, 6.0 mole % oxygen, 1.1 mole % $CO_2$, and 2.1 ppmv ethyl chloride is introduced to a high efficiency, rhenium-promoted silver catalyst loaded into a pilot plant reactor with a tube volume of 0.098 ft$^3$. The reactor pressure is 295 psig, and the total feed gas flow rate is 680 scfh. The reaction temperature is 230° C. at the start of run and for the first 5 days on-stream. The temperature is 226° C. from days 6-10, and 222° C. from days 13-38. Δ EO is typically 2.2% throughout the run. From day 6 on stream (2.0 klb/ft$^3$ (0.032 kT/m$^3$) cumulative EO production), the feed composition is 35 mole % ethylene, 8.5 mole % oxygen, 1% $CO_2$, and 0.6 mole % ethane. The results are shown in FIGS. 6A-6B.

On day 1 on-stream, the molar ratio of oxygen to ethylene is 0.22. On day 3, the molar ratio is raised to 0.23, and on day 5 the molar ratio is raised to 0.24. The reactor trips on days 4, 7, 8, 14, 17, and 23. However, performance is not adversely affected, and the efficiency remains at 87.4% or higher throughout the run, which is believed to be attributable to the maintenance of a molar ratio of oxygen to ethylene of at least 0.2.

Example 4

A feed gas comprising ethylene, oxygen, and ethyl chloride is introduced to a high efficiency, rhenium-promoted silver catalyst loaded into a pilot plant reactor. Two different runs are performed with different start-up molar ratios of oxygen to ethylene. The results are shown in FIGS. 7A-7B.

The first run (identified as "Rx1-2" in FIGS. 7A-7B) is carried out at a start-up molar ratio of oxygen to ethylene of 0.15 which is reached by day 1 on stream (0.2 klb/ft$^3$ (0.003 kT/m$^3$) cumulative EO production). The feed composition at this point is 40 mole % ethylene, 0.6 mole % ethane, 6 mole % oxygen, 2.0 mole % $CO_2$, and 2.4 ppmv ECl, with the balance being nitrogen. The molar ratio is raised to 0.17 on day 2 (0.5 klb/ft$^3$ (0.008 kT/m$^3$) cumulative EO production) and to 0.21 on day 3 (0.8 klb/ft3 (0.013 kT/m$^3$) cumulative EO production) by progressively increasing the oxygen concentration to 8.5 mole %. Between days 14 to 20, the oxygen to ethylene molar ratio in the feed is increased to 0.28 by decreasing the ethylene concentration. The initial start-up reaction temperature is 222° C., and the initial start-up value of Z* is 2.4. On day 3 the reaction temperature is increased to 225° C. and Z* drops to 2.3. On day 13, the reaction temperature is increased to 230° C., and Z* is increased to 3.1. Efficiency remains consistently above 87.0% thereafter for the next 16 days on stream. The initial reaction temperature is 222° C., and the initial Z* is 2.4.

The second run (identified as "Rx2-7" in FIGS. 7A-7B) is carried out at a start-up molar ratio of oxygen to ethylene between 0.05 and 0.1 and is held there for three days on-stream (0.7 klb/ft$^3$ (0.011 kT/m$^3$) cumulative EO production). On day 4, the molar ratio is raised to 0.13, and from day 5 onward the molar ratio is increased to 0.20. The feed composition is 35 mole % ethylene, 0.3 mole % ethane, and 1 mole % $CO_2$, The oxygen concentration is between 1.9-3.0 mole % over the first 3 days on stream and is later increased to 7.2 mole % by day 5 on stream. The initial reaction temperature is 230° C., and the initial Z* is 2.0. On day 2, the reaction temperature is decreased to 222° C., and Z* decreases to 1.7 from days 2-8. Efficiency is initially 84.8% and then drops to 83.4%. Following the adjustment of the molar ratio of oxygen to ethylene to 0.2, the efficiency increases to 85.5%. Δ EO is 2.1% for both runs. Although the molar ratios for both runs are ultimately comparable, run 1 ultimately achieves a higher efficiency, which is believed to be attributable to its relatively faster attainment of a molar ratio of oxygen to ethylene of at least 0.2, as well as to its reaction temperature and Z* values.

Example 5

A feed gas comprising ethylene, oxygen, and ethyl chloride is introduced to a high-efficiency, rhenium-promoted silver catalyst loaded in a pilot plant reactor having a tube volume of 0.183 ft$^3$. The feed composition at the beginning of start-up is 5 mole % oxygen, 1 mole % $CO_2$, 25 mol % ethylene, 0.6 mol % ethane, and 2.9 ppmv ECl. The start-up ICT is 214° C. The initial start-up Z* is 3.0, and the initial start-up oxygen to ethylene molar ratio is 0.20. The start-up value of Z* does not conform to Equation (6), which yields a Z* value of 0.3 at an ICT of 214° C. The reactor pressure is 260 psig, and the total feed gas flow is 890 scfh. The reactor is operated on automatic temperature control. Between days 3-5 on stream, the oxygen to ethylene molar ratio is 0.15, which is achieved by progressively increasing the ethylene concentration to 33 mole %. Thereafter, the oxygen to ethylene molar ratio is increased to 0.2 by decreasing the ethylene concentration in the feed to 25 mol % and is then progressively increased to 0.43 by increasing the oxygen concentration and decreasing the ethylene concentration between days 9 and 23 on stream. The feed composition from day 24 on stream is substantially 30 mole % ethylene, 7.3 mole % oxygen, 1.3 mole % $CO_2$, and 0.6 mole % ethane. On day 8, the ICT is raised to 225° C. and is maintained between 223° C. and 225° C. subsequently. Z* is typically close to 2.0. The results are shown in FIGS. 8A-8B.

The catalyst starts with low selectivity due to poor selection of the temperature and Z*. Decreasing oxygen to ethylene molar ratio to 0.15 further deteriorates efficiency up to day 5 on stream. Restoring temperature and Z* to adequate values while maintaining the molar ratio of oxygen to ethylene above 0.2 yields an improvement in efficiency. The temporary increase of the molar ratio of oxygen to ethylene to a value of 0.43 (by decreasing the ethylene concentration) is believed to yield an improvement in efficiency that is seen after the molar ratio is dropped back down to 0.24. This example illustrates that the efficiency toward the alkylene oxide can be improved by adjusting the process from an initial condition in which at least one of the molar ratio of oxygen to alkylene, reaction temperature, and Z* is outside of its respective preferred range of at least 0.2, from 215° C. to 240° C., and from 1.0 to 5.0 to a second condition in which each of the molar ratio of oxygen to ethylene, reaction temperature, and Z* is within its respective, foregoing preferred range.

Example 6

A feed gas comprising ethylene, oxygen, and ethyl chloride is introduced to a continuous stirred tank reactor loaded with a high-efficiency, rhenium-promoted silver catalyst. Various runs are conducted in which temperature, Z*, or the molar ratio of oxygen to ethylene are varied while the other two variables are held constant. The results are shown in FIGS. 9A-9H. The process variable values shown in the various figures are summarized in Table 1 below:

| Figure | Molar Ratio of oxygen to ethylene | Reaction Temperature (T° C.) | Z* |
|---|---|---|---|
| 9A | 0.23 | 225, 230 | 1.5 |
| 9B | 0.23 | 225, 230 | 2.0 |
| 9C | 0.23 | 225° C. | 1.0, 1.2, 1.5, 2.0 |
| 9D | 0.23 | 230° C. | 1.5, 2.0, 2.5 |
| 9E | 0.23, 0.27, 0.32, 0.53, 1.60 | 225° C. | 1.0-2.0 |
| 9F | 0.23, 0.32, 0.53 | 230° C. | 1.0-2.0 |
| 9G | 0.23, 0.53, 1.60 | 225° C. | 2.0 |
| 9H | 0.23, 0.32, 0.53 | 230° C. | 2.0 |

The data presented in FIGS. 9C-9D indicates that better efficiency is realized at a Z* of 1.5 and 2 at 230° C. relative to 225° C. when the molar ratio is 0.23. Increasing Z* at a constant temperature and molar ratio appears to have a detrimental effect on efficiency. The data in FIGS. 9G and 9H indicate that a molar ratio of 0.23 achieves better efficiencies at a temperature of 230° than at a temperature of 225° C.

Example 7

A feed gas comprising 35 vol % ethylene, 3 to 4 vol % oxygen, 0 to 1 vol % carbon dioxide, and 0.4 vol % ethane, is fed to a Rotoberty reactor containing 40 cm$^3$ of a high-efficiency, rhenium-promoted silver catalyst. The gas hourly space velocity is 6700 h$^{-1}$. The reactor pressure is 285 psig. The initial value of Z* is 6.5. The initial reaction temperature (ICT) ranges from 210° C. to 213.8° C. The initial value of the molar oxygen to ethylene ratio ranges from 0.085 to 0.114. The initial conditions are maintained until the cumulative ethylene oxide production (from start-up) is 0.036 kT/m$^3$. The resulting efficiency toward ethylene oxide is 81.8%, and ΔEO is 1.21 vol. %.

At this point, the process is adjusted to a second condition wherein reaction temperature is increased to 230° C., Z* is lowered to 3.5, and the feed gas composition is slightly adjusted to 35 vol % ethylene, 4 vol % oxygen, and 1.25 vol % carbon dioxide, yielding a molar ratio of oxygen to ethylene of 0.11. The second condition is maintained until the cumulative ethylene oxide production (from start-up) reaches 0.0415 kT/m$^3$.

The process is then adjusted to a third condition wherein the reaction temperature is increased to 235° C., and the feed gas composition is adjusted to 30 vol % ethylene, 0.4 vol % ethane, 1.5 vol % carbon dioxide, and 6 vol % oxygen. The other process parameters remain at the same values as in the second condition. The resulting molar of oxygen to ethylene is 0.2.

The results of the foregoing process adjustments are depicted in FIGS. 10A-10C. Each figure provides cumulative ethylene oxide production data As the figures indicate, following the adjustment of the process to the third condition, a ΔEO value of 2.35 vol % and an efficiency toward ethylene oxide of 78.1% are observed at a cumulative ethylene oxide production rate of 0.0423 kT/m$^3$. The process then shows continuous improvement, with the efficiency toward ethylene oxide increasing from 78.1% to 79.5% and ΔEO remaining substantially at 2.31 vol % until cumulative ethylene oxide production reaches 0.049 kt/m$^3$, after which the process is shut down.

What is claimed is:

1. A method for starting-up an alkylene oxide production process, the alkylene oxide production process comprising reacting a feed gas comprising an alkylene, oxygen, and at least one organic chloride over a high efficiency silver catalyst to yield a reaction product comprising the alkylene oxide, the start-up method comprising:
providing a feed gas comprising the alkylene, oxygen, and the at least one organic chloride, wherein the feed gas has an overall chloriding effectiveness represented by the formula:

$$Z^* = \frac{\text{ethyl chloride equivalent (ppmv)}}{\text{ethane equivalent (mole \%)}}$$

wherein the ethyl chloride equivalent is the total concentration in ppmv of ethyl chloride which provides the same catalyst chloriding effectiveness of the at least one organic chloride in the feed gas at the concentration of the at least one organic chloride in the feed gas, the ethane equivalent is the total concentration in mole % of ethane which provides the same dechloriding effectiveness as the non-chloride containing hydrocarbons in the feed gas at the concentration of the non-chloride containing hydrocarbons in the feed gas, and the feed gas has a Z* value ranging from 1.0 to 5.0;
reacting the feed gas over the high-efficiency silver catalyst at a reaction temperature such that within a catalyst aging period of no greater than 0.03 kT alkylene oxide/m$^3$ catalyst after the reactor is first on-stream, the reaction temperature is from 215° C. to 240° C., and the molar ratio of oxygen to the alkylene in the feed gas is at least 0.2, thereby yielding a reaction product comprising a start up concentration of the alkylene oxide.

2. The method of claim 1, further comprising selecting a target alkylene oxide concentration in the reaction product and maintaining the molar ratio of oxygen to alkylene of at least 0.2 no longer than until the start-up concentration of the alkylene oxide in the reaction product is equal to the target concentration of the alkylene oxide in the reaction product.

3. The method claim 2, wherein the step of maintaining the molar ratio of oxygen to the alkylene in the feed gas of at least 0.2 is conducted no longer than until the efficiency of the process to the alkylene oxide is at least 85%.

4. The method of claim 2, wherein the step of maintaining the molar ratio of oxygen to the alkylene in the feed gas of at least 0.2 is conducted no longer than until the start-up concentration of the alkylene oxide in the reaction product is at least 1.5 mole %.

5. The method of claim 1, wherein the step of adjusting both the reaction temperature and the overall chloriding effectiveness comprises adjusting at least one of the reaction temperature and Z* according to the following relationship:

$$Z^* = (T_{rx} - T_o)/S_o$$

wherein, $T_{rx}$ is the reactor coolant inlet temperature in ° C., $T_o$ is the temperature-axis intercept calculated by extrapolating a plot of Z* versus $T_{rx}$ to Z*=0, and $S_o$ is a slope relating the change in inlet coolant temperature to the corresponding change in Z*.

6. The method of claim 1, wherein within a catalyst aging period of no greater than 0.02 kT alkylene oxide/m$^3$ catalyst after the reactor is first on-stream, the reaction temperature is from 225° C. to 235° C.

7. The method of claim 1, wherein within no more than 5 hours after the reactor is first on stream, the molar ratio of oxygen to the alkylene in the feed gas is at least 0.15.

8. The method of claim 1, wherein within a catalyst aging period of no greater than 0.02 kT alkylene oxide/m$^3$ catalyst after the reactor is first on-stream, the molar ratio of oxygen to the alkylene in the feed gas is no more than 0.35.

9. A method for producing an alkylene oxide by reacting an alkylene, oxygen, and at least one organic chloride over a high efficiency silver catalyst, the method comprising:

reacting a feed gas comprising the alkylene, oxygen, and at least one organic chloride over the high-efficiency silver catalyst at a reaction temperature and an overall chloriding effectiveness to yield a reaction product comprising the alkylene oxide such that the process has a molar ratio of oxygen to the alkylene in the feed gas and a first efficiency to the alkylene oxide, the first efficiency to the alkylene oxide being less than a target efficiency to the alkylene oxide;

adjusting at least one process parameter such that the efficiency of the process to the alkylene oxide increases from the first efficiency to a second efficiency, wherein the at least one process parameter is selected from the group consisting of the molar ratio of oxygen to the alkylene in the feed gas, reactor temperature, and overall chloriding effectiveness, following the adjusting step the molar ratio of oxygen to the alkylene in the feed gas is at least 0.2, the reaction temperature is from 215° C. to 240° C., the overall chloriding effectiveness is represented as $Z^*$ and is from 1.0 to 5.0, and $Z^*$ is represented as follows:

$$Z^* = \frac{\text{ethyl chloride equivalent}\,(ppmv)}{\text{ethane equivalent (mole \%)}}$$

wherein the ethyl chloride equivalent is the total concentration in ppmv of ethyl chloride which provides the same catalyst chloriding effectiveness of the at least one organic chloride in the feed gas at the concentration of the at least one organic chloride in the feed gas, and the ethane equivalent is the total concentration in mole % of ethane which provides the same dechloriding effectiveness as the non-chloride containing hydrocarbons in the feed gas at the concentration of the non-chloride containing hydrocarbons in the feed gas.

10. The method of claim 9, wherein the at least one process parameter includes reaction temperature, and the step of adjusting the reaction temperature comprises adjusting the reaction temperature from a value outside the range of 225° C. to 235° C. to a value inside the range of 225° C. to 235° C.

11. The method of claim 9, wherein the at least one process parameter includes the molar ratio of oxygen to alkylene in the feed gas, and the step of adjusting the molar ratio of oxygen to alkylene in the feed gas comprises adjusting the molar ratio from a first value of less than 0.2 to a second value of at least 0.2.

12. The method of claim 9, wherein the second efficiency to the alkylene oxide is at least 85%.

13. The method of claim 9, wherein following the adjusting step the molar ratio of oxygen to the alkylene in the feed gas is no more than 0.35.

14. The method of claim 9, wherein the at least one process parameter includes $Z^*$, and the step of adjusting $Z^*$ comprises adjusting $Z^*$ from a first value outside the range of from 1.0 to 5.0 to a second value inside the range of from 1.0 to 5.0.

15. The method of claim 9, wherein the at least one process parameter includes the molar ratio of oxygen to alkylene in the feed gas, reaction temperature, and $Z^*$, the step of adjusting the molar ratio of oxygen to alkylene in the feed gas comprises adjusting the molar ratio from a first value of less than 0.2 to a second value of at least 0.2, the step of adjusting the reaction temperature comprises adjusting the reaction temperature from a first value outside the range of from 215° C. to 240° C. to a second value inside the range of from 215° C. to 240° C., and the step of adjusting $Z^*$ comprises adjusting $Z^*$ from a first value outside the range of from 1.0 to 5.0 to a second value inside the range of from 1.0 to 5.0.

* * * * *